United States Patent [19]

Denny et al.

[11] Patent Number: 5,985,909
[45] Date of Patent: Nov. 16, 1999

[54] CYCLOPROPYLINDOLES AND THEIR SECO PRECURSORS, AND THEIR USE AS PRODRUGS

[75] Inventors: William Alexander Denny; Moana Tercel, both of Auckland, New Zealand

[73] Assignee: Cancer Research Campaign Technology Limited, United Kingdom

[21] Appl. No.: 09/011,883

[22] PCT Filed: Aug. 19, 1996

[86] PCT No.: PCT/NZ96/00083

§ 371 Date: Feb. 18, 1998

§ 102(e) Date: Feb. 18, 1998

[87] PCT Pub. No.: WO97/07097

PCT Pub. Date: Feb. 27, 1997

[30] Foreign Application Priority Data

Aug. 18, 1995 [GB] United Kingdom .................. 9516943

[51] Int. Cl.⁶ ..................... A61K 31/40; C07D 209/14
[52] U.S. Cl. ............................... 514/414; 548/455
[58] Field of Search ............................ 548/455; 514/414

[56] References Cited

FOREIGN PATENT DOCUMENTS

| A 415 731 | 3/1991 | European Pat. Off. . |
| 93/08288 | 4/1993 | WIPO . |
| 93/11099 | 6/1993 | WIPO . |
| 94/02450 | 2/1994 | WIPO . |
| 95/12678 | 5/1995 | WIPO . |

OTHER PUBLICATIONS

Culver, et al., "In Vivo Gene Transfer With Retroviral Vector–Producer Cells For Treatment Of Experimental Brain Tumors," *Science* (1992) vol. 256:1550–1552.

Englehardt, et al., "Direct Gene transfer Of Human CFTR Into Human Bronchial Epithelia Of Xenografts With E1–Deleted Adenviruses," *Nature Genetics* (1993) vol. 4:27–34.

Huber, et al., "Retroviral–Mediated Gene Therapy For The Treatment Of Hepatocellular Carcinoma: An Innovative Approach For Cancer Therapy," *Proc. Nat'l. Acad. Sci., USA* (1991) vol. 88:8093–8043.

Knox, et al., "Bioactivation Of CB 1954: Reaction Of The Active 4–Hydroxylamino Derivative With Thioesters To Form The Ultimate DNA–DNA Interstrand Crosslinking Species," *Biochemical Pharmacology* (1991) vol. 42:1691–1697.

Knox, et al., The Bioactive Of 5–(Aziridin–1–yl)–2,4–Dinitrobenzamide (CB1954)–II, A Comparison Of An *Escherichia Coli* Nitroeductase And Walker DT Diaphorase, *Biochemical Pharmacology* (1992) vol. 44: 2297–2301.

Mauger, et al., "Self–Immolative Prodrugs: Candidates For Antibody–Directed Enzyme Prodrug therapy In Conjunction With A Nitroductase Enzyme," *J. Med. Chem.* (1994) vol. 37:3452–3458.

Ram, et al., "In Situ Retroviral–Mediated Gene Transfer For The Treatment Of Brain Tumors In Rats," *Cancer Research* (1993) vol. 53:83–88.

*Primary Examiner*—Robert W. Ramsuer
*Attorney, Agent, or Firm*—Pamela J. Sherwood; Bozicevic, Field & Francis LLP

[57] ABSTRACT

The present invention provides compounds of formula (I) and (II) which may be used as anticancer drugs.

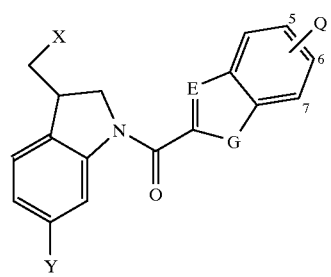

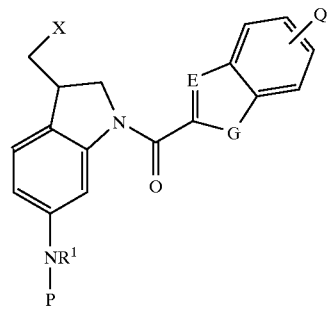

12 Claims, No Drawings

CYCLOPROPYLINDOLES AND THEIR SECO PRECURSORS, AND THEIR USE AS PRODRUGS

The present invention relates to novel amino analogues of the general class of cyclopropylindoles and their seco precursors, and is particularly concerned with the use of these compounds as prodrugs for antibody-directed enzyme-prodrug therapy (ADEPT) and gene-directed enzyme-prodrug therapy (GDEPT) for cancer.

BACKGROUND TO THE INVENTION

The use of prodrugs represents a clinically very valuable concept in cancer therapy since, particularly where the prodrug is to be converted to an anti-tumour agent under the influence of an enzyme that is linkable to a monoclonal antibody that will bind to a tumour associated antigen, the combination of such a prodrug with such an enzyme monoclonal/antibody conjugate represents a very powerful clinical agent. This approach to cancer therapy, often referred to as "antibody directed enzyme/prodrug therapy" (ADEPT) is disclosed in WO88/07378.

A further therapeutic approach termed "virus-directed enzyme prodrug therapy" (VDEPT) has been proposed as a method for treating tumour cells in patients using prodrugs. Tumour cells are targeted with a viral vector carrying a gene encoding an enzyme capable of activating a prodrug. The gene may be transcriptionally regulated by tissue specific promoter or enhancer sequences. The viral vector enters tumour cells and expresses the enzyme, in order that a prodrug is converted to an active drug within the tumour cells (Huber et al, Proc. Natl. Acad. Sci. USA (1991) 88, 8039). Alternatively, non-viral methods for the delivery of genes have been used. Such methods include calcium phosphate co-precipitation, microinjection, liposomes, direct DNA uptake, and receptor-mediated DNA transfer. These are reviewed in Morgan & French, Annu. Rev. Biochem., 1993, 62;191. The term "GDEPT" (gene-directed enzyme prodrug therapy) is used to include both viral and non-viral delivery systems.

Cyclopropylindole compounds are a class of highly potent antitumour antibiotics with the natural products CC-1065 (V. L. Reynolds et al, J. Antibiot., 39, 1986, 319–334) and the duocarmycins (D. L. Boger, Pure & Appl. Chem., 66, 1994, 837–844), having IC50's in the low pM range. These compounds bind in the minor groove of DNA and alkylate in a highly sequence selective manner at N-3 of adenine (D. L. Boger et al, Tetrahedron, 47, 1991, 2661–2682). Studies with compounds that model the alkylation subunit have shown that the more stable open chain seco precursors are as potent as the cyclopropylindole compounds. Further, ring closure is not essential for DNA alkylation, and there is some measure of electronic control by the both the 6-substituent (D. L. Boger et al, J. Am. Chem. Soc., 113, 1991, 3980–3983) and the 1-substituent (D. L. Boger and W. Yun, J. Am. Chem. Soc., 116, 1994, 5523–5524)-on the rate of alkylation.

A number of synthetic analogues of the natural products have been prepared in which the oxygen substituent is protected as a carbamate that must be cleaved (by non-specific enzymatic hydrolysis) for activity. These compounds include carzelesin (L. H. Li et al, Cancer Res., 52, 1992, 4904–4913) having the structure A:

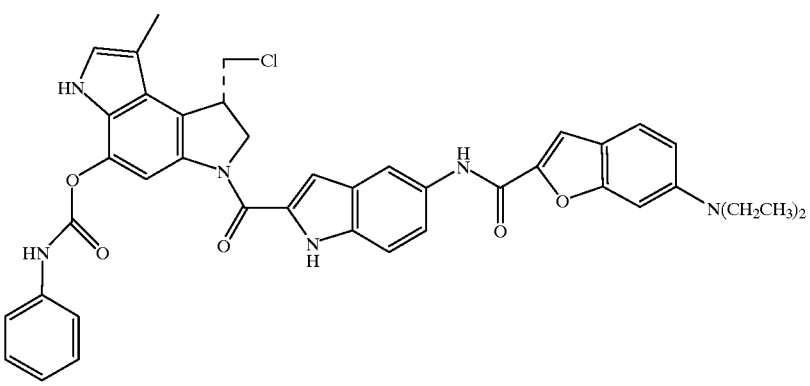

(A)

A related compound is KW-2189 (E. Kobayashi et al, Cancer Res., 54, 1994, 2404–2410) which has the structure B:

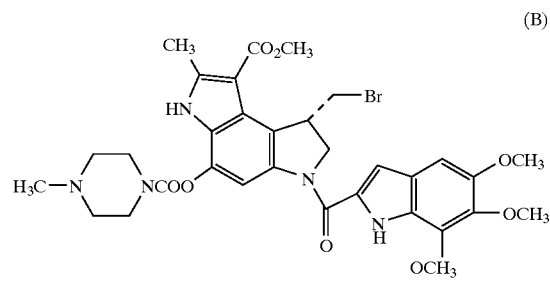

(B)

Both carzelesin and KW-2189 show anticancer activity against a range of human tumours and are in clinical trial. Further analogues of a similar type are disclosed in WO88/04659 and WO091/16324.

DISCLOSURE OF THE INVENTION

In one aspect, the present invention relates to the new class of substituted seco indolines, represented by formula (I):

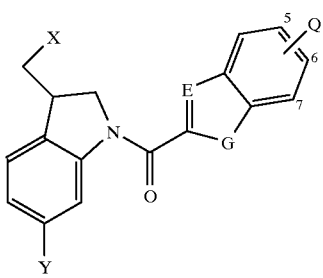
(I)

wherein:

X is halogen or $OSO_2R$, where R represents H or lower straight or branched alkyl (up to five carbon atoms) optionally substituted with from 1 to 4 hydroxyl, acid (COOH) or amino groups which amino groups are optionally substituted by one or two lower alkyl groups;

Y is $NH_2$, $NO_2$, NHOH, NHR, NRR, N(O)RR, NROH, SR or SSR, where R is defined as above, but that in the case where Y is SSR, then R can also be another moiety of formula (I) (i.e., a symmetrical disulfide);

E is —N= or —CH=;

G is O, S or NH; and

Q is from one to three of H, OR, NRR, CONHR, NHCOR or NHCONHR at any one of positions 5 to 7 where R is defined as above (which may be the same or different when Q is two or three), a group of formula (Ia):

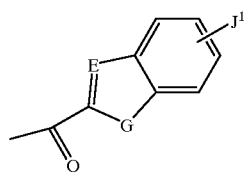
(Ia)

where E and G are as defined above, $J^1$ is up to three groups, H, OR, NRR, CONHR or NHCOR (which may be the same or different when $J^1$ is two or three) where R is as defined above, or is a group of the formula —$CONHJ^2$, —$NHJ^2$ or —$OJ^2$ where $J^2$ is a group —$(CH_2)_m$Ht where m is an integer from 1 to 4 and Ht is a carbon or heterocyclic ring containing 5 or 6 atoms, one or two of which may be oxygen, sulphur or nitrogen (the remainder being carbon);

or a physiologically functional derivative thereof.

In a second aspect, the present invention relates to the class of compounds represented by formula (II):

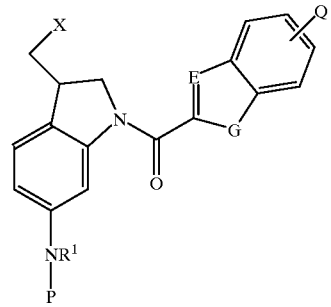
(II)

wherein:

X, Q, E and G are as defined above for formula (I), $R^1$ is a group R as defined above and P is selected from the structures of formulae (IIa, IIb or IIc):

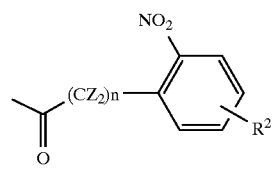
(IIa)

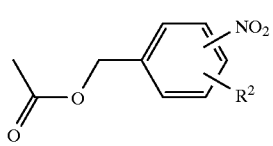
(IIb)

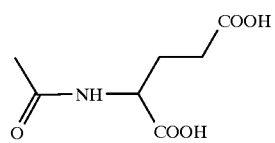
(IIc)

wherein:

Z is H or Me;

n is 1 or 2; and $R^2$ is a group R, CONHR, NHCOR, OR or $SO_2R$, where R is as defined above;

or a physiologically functional derivative thereof.

It is recognised that compounds of formulae (I), (II) and (IIa–c) may exist in different enantiomeric or diastereomeric forms. In such cases it is to be understood that the above formulae represent any possible enantiomeric or diastereomeric form or a mixture thereof.

A halogen group means a fluoro, chloro, bromo or iodo group. A chloro group is preferred. Preferred compounds of formulae (I) and (II) include those in which X represents Cl. It is preferred that Q represents H or 5,6,7-triOMe and P represents formula IIb, where $R^2$ represents H or CONHR, where R is defined as above. It is preferred that where Q represents a group of the formula (Ia) it is attached at the 5- or 6-positions.

Preferred values of Q include:
—$CONHCH_2CH_2$Nmorpholide,
—CONHCH $(CH_2OH)_2$,
—$CONHCH_2CH_2$(2-pyridyl),
—$CONHCH_2CH_2N$ $(Me)_2$,
—$CONHCH_2CH_2CH_3$, —CONHCH$_2$CH$_2$COOH,
—NHCOCH$_2$CH$_2$N (Me)$_2$, and
—NHCOCH$_2$CH$_2$COOH.

When J$^2$ is a group —(CH$_2$)$_m$Ht m is preferably 2 and Ht is preferably a 5 or 6 membered carbon ring or a 5 or 6 membered ring containing one oxygen and/or one nitrogen which are not adjacent when both are present, and is most preferably Nmorpholide (i.e. a morpholino group attached at the nitrogen) or pyridyl.

These groups are desirably linked to the 5 or 6 position of the formula (I) or (II) nucleus.

The group R$^1$ in formula (II) is preferably hydrogen or methyl.

It is preferred that when P is a group (IIb) the nitro group is in the 4- (para) or 2-position. The 4-position is preferred.

In another aspect, the present invention relates to the use of the compounds of formulae (I) and (II) as anticancer drugs. The compounds may be used for the selective killing of oxic and hypoxic tumour cells in methods of treatment of cancers for example leukaemias, and particularly solid cancers including breast, bowel and lung tumours, including small cell lung carcinoma.

In a further aspect, the present invention relates to the use of the compounds of formula (II), in conjunction the nitroreductase or carboxypeptidase enzymes (for example isolated from *E. coli*) in methods of ADEPT or GDEPT therapy. Compounds of the formula (I) in which Y is NO$_2$ or N(O)RR may also be used in conjunction with nitroreductase.

The invention also provides pharmaceutical compositions comprising a compound of the formula (I) or the formula (II) together with a pharmaceutically acceptable carrier or diluent.

DETAILED DESCRIPTION OF THE INVENTION

A. Synthesis of Compounds of the Formula (I)

The compounds of formula (I) can be prepared by the processes outlined for specific examples in Schemes 1 and 2. In Scheme 1, 4-chloro-3-nitrobenzoic acid is converted to its t-butyl ester and condensed with the sodium salt of dimethyl malonate. The t-butyl ester is cleaved and the resulting acid is subjected to Curtius rearrangement to give the Cbz-protected aniline. Reduction of the malonate with diisobutylaluminium hydride yields the corresponding diol. The nitro group is then selectively reduced by hydrogenation over platinum oxide. Protection of the resulting amine with di-t-butylcarbonate, followed by cyclisation with diethylazodicarboxylate forms the indoline ring. The hydroxymethyl group at the 3-position is converted to a sulphonate by reaction with RSO$_2$Cl (when X is SO$_2$R; in the example of scheme 1, R is CH$_3$), and the Boc protecting group cleaved by HCl. The resulting unstable amine hydrochloride is immediately coupled with the appropriate carboxylic acid (in the example of Scheme 1, 5,6,7-trimethoxyindole-2-carboxylic acid is used, illustrating the case where E is —CH=, G is NH and Q is 5,6,7-trimethoxy). The Cbz protecting group is removed by hydrogenolysis. The mesylate is displaced by the group X (in the case of Scheme 1 by chloride) by reaction with lithium halide (when X is halogen).

In Scheme 2, the t-butyl ester of 2-chloro-5-nitrobenzoic acid is condensed with dimethyl malonate, and converted to the free acid using the same procedure as in Scheme 1. Reaction with diphenylphosphoryl azide in the presence of triethylamine leads directly to the 2-indolone, via intramolecular trapping of the intermediate isocyanate. Reduction with borane gives the corresponding indoline, and the indoline nitrogen is protected with the Boc group. Treatment of the diester with sodium methoxide results in decarboxymethylation to give the monoester derivative, which is reduced with diisobutylaluminium hydride. The resulting alcohol is treated with RSO$_2$Cl (when X is OSO$_2$R) and then displaced with lithium halide (when X is halogen). In Scheme 2, treatment with lithium chloride is shown to provide the chloro compound, which is coupled with the appropriate carboxylic acid (in the example of Scheme 1, 5,6,7-trimethoxyindole-2-carboxylic acid is used, illustrating the case where E is —CH=, G is NH and Q is 5,6,7-trimethoxy).

Reduction of the 6-nitro group by hydrogenation over platinum oxide then gives the compound of the formula I where Y is NH$_2$.

B. Synthesis of Compounds of the Formula (II)

The compounds of formula (IIa) and (IIb) may be prepared by reaction of compounds of the formula (I) with a reactive derivative of the group P, for example the acid chloride derivative of (IIa) or the chloroformate derivative of (IIb). Such reactive intermediates may be made from the carboxylic acid derivatives of (IIa) or alcohol derivatives of (IIb). Such reactive derivatives may be made from carboxylic acids of the formula P-H (where P is as defined above). The carboxylic acids and alcohols may be made by chemistry known per se. Some compounds are commercially available. Scheme 1 illustrates this with 4-nitrobenzylchloroformate.

Compounds of the formula (IIc) may be made by coupling glutamic acid derivatives, such as isocyanates, with compounds of the formula (II) in which P is hydrogen. The carboxy groups of glutamic acid may be protected by esterification with C$_{1-6}$ alkyl protecting groups, the t-butyl ester groups being preferred. Where such ester groups are used, they may be removed after reaction of the glutamic acid derivative with the compound of formula (I) by hydrolysis. In some cases this may result in racemisation.

Reference may be made to, for example, WO88/07378 and WO91/03460 for appropriate reaction conditions for production of glutamic acid derivatives of compounds of formula (II).

Reference may also be made to the synthetic routes disclosed in WO88/04659 and WO91/16324 especially those in which Q is a group of the formula (Ia). Analogous routes may be used to make compound of the present invention.

C. GDEPT

C(i)—Vector Systems

In general, the vector for use in GDEPT therapies may be any suitable DNA or RNA vector.

Suitable viral vectors include those which are based upon a retrovirus. Such vectors are widely available in the art. Huber et al (ibid) report the use of amphotropic retroviruses for the transformation of hepatoma, breast, colon or skin cells. Culver et al (Science (1992) 256; 1550–1552) also describe the use of retroviral vectors in GDEPT. Such vectors or vectors derived from them may also be used. Other retroviruses may also be used to make vectors suitable for use in the present invention. Such retroviruses include rous sarcoma virus (RSV).

Englehardt et al (Nature Genetics (1993) 4; 27–34) describe the use of adenovirus based vectors in the delivery of the cystic fibrosis transmembrane conductance product (CFTR) into cells, and such adenovirus based vectors may also be used. Vectors utilising adenovirus promoter and other control sequences may be of use in delivering a system according to the invention to cells in the lung, and hence useful in treating lung tumours.

Other vector systems including vectors based on the Molony murine leukaemia virus are known (Ram, Z et al, Cancer Research (1993) 53;83–88; Dalton & Treisman, Cell (1992) 68; 597–612). These vectors contain the Murine Leukaemia virus (MLV) enhancer cloned upstream at a β-globin minimal promoter. The β-globin 5' untranslated region up to the initiation ATG is supplied to direct efficient translation of the enzyme.

Suitable promoters which may be used in vectors described above, include MLV, CMV, RSV and adenovirus promoters. Preferred adenovirus promoters are the adenovirus early gene promoters. Strong mammalian promoters may also be suitable. An example of such a promoter is the EF-1α promoter which may be obtained by reference to Mizushima and Nagata ((1990), Nucl. Acids Res. 18; 5322). Variants of such promoters retaining substantially similar transcriptional activities may also be used.

C(ii)—Nitroreductase

Compounds of the formula (II) in which P is a group (IIa) or (IIb) can be activated by removal of the group P by nitroreductase.

Preferably, the enzyme is a non-mammalian nitroreductase enzyme, such as a bacterial nitroreductase. An *E.coli* nitroreductase as disclosed in WO93/08288 is particularly preferred. The enzyme may be modified by standard recombinant DNA techniques, e.g. by cloning the enzyme, determining its gene sequence and altering the gene sequence by methods such as truncation, substitution, deletion or insertion of sequences for example by site-directed mutagenesis. Reference may be made to "Molecular Cloning" by Sambrook et al (1989, Cold Spring Harbor) for discussion of standard recombinant DNA techniques. The modification made may be any which still leaves the enzyme with the ability to reduce the nitro group of the protecting group P in formula II or the nitro or amine N-oxide groups when these are represented by Y in formula I but alters other properties of the enzyme, for example its rate of reaction or selectivity.

In addition, small truncations in the N- and/or C-terminal sequence may occur as a result of the manipulations required to produce a vector in which a nucleic acid sequence encoding the enzyme is linked to the various other vector sequences.

C(iii) Carboxypeptidase

Compounds of the formula (II) in which P is a group (IIc) can be activated by removal of the group P by a carboxypeptidase enzyme.

The enzyme is preferably a bacterial carboxypeptidase, especially carboxypeptidase CPG2 or Pseudomonas γ-glutamylhydrolase EC3.4.22.12 (Levy CC & Goldman P J. Biol. Chem. 242; p2933 (1967).

Carboxypeptidase G2 (CPG2) is disclosed in WO88/07378. Although native CPG2 is preferred, alterations to its sequence which are amino acid substitutions, deletions or insertions (eg. of about 1, 2, 3, 4, 5, 10 or 20 residues in each case) are also possible. In any event, the alteration will be such that the enzyme retains its ability to convert a prodrug to an active drug at substantially the same rate as the native enzyme. In this context, "substantially the same rate" will desirably be within 1 order of magnitude, and preferably from about 50-fold e.g. about 2-fold less to 2, 5 or 10 fold more.

In addition to specific changes the enzyme may otherwise be altered by truncation, substitution, deletion or insertion as long as the activity of the enzyme is substantially unchanged as defined above. For example, small truncations in the N- and/or C-terminal sequence may occur as a result of the manipulations required to produce a vector in which a nucleic acid sequence encoding the enzyme is linked to a suitable promoter.

D. Adept

For applications in ADEPT systems, an antibody directed against a tumour specific marker is linked to the nitroreductase or carboxypeptidase enzyme, which may be modified as described above. The antibody may be monoclonal or polyclonal. For the purposes of the present invention, the term "antibody", unless specified to the contrary, includes fragments of whole antibodies which retain their binding activity for a tumour target antigen. Such fragments include Fv, F(ab') and F(ab')$_2$ fragments, as well as single chain antibodies. Furthermore, the antibodies and fragments thereof may be humanised antibodies, eg. as described in EP-A-239400.

The antibodies may be produced by conventional hybridoma techniques or, in the case of modified antibodies or fragments, by recombinant DNA technology, eg by the expression in a suitable host vector of a DNA construct encoding the modified antibody or fragment operably linked to a promoter. Suitable host cells include bacterial (eg. *E.coli*), yeast, insect and mammalian. When the antibody is produced by such recombinant techniques the enzyme may be produced by linking a nucleic acid sequence encoding the enzyme (optionally modified as described above) to the 3' or 5' end of the sequence of the construct encoding the antibody or fragment thereof.

E. Physiologically Functional Derivatives

Physiologically functional derivatives of prodrugs include salts, amides and esters. Esters include carboxylic acid esters in which the non-carbonyl moiety of the ester grouping is selected from straight or branched chain $C_{1-6}$alkyl, (methyl, n-propyl,, n-butyl or t-butyl); or $C_{3-6}$cyclic alkyl (e.g. cyclohexyl). Salts include physiologically acceptable base salts, eg derived from an appropriate base, such as alkali metal (e.g. sodium), alkaline earth metal (e.g. magnesium) salts, ammonium and $NR_{4'''}$ (wherein R' is $C_{1-4}$ alkyl) salts. Other salts include acid addition salts, including the hydrochloride and acetate salts. Amides include non-substituted and mono- and di-substituted derivatives. Such derivatives may be prepared by techniques known per se in the art of pharmacy.

Other physiologically functional derivatives may occur by formation of such derivatives in the body after administration of the compounds of the invention.

For example, many of the compounds of formula (I) and (II), particularly those where Y is $NH_2$ or NHR may be cytotoxic via a cyclopropylimine structure of formula (III):

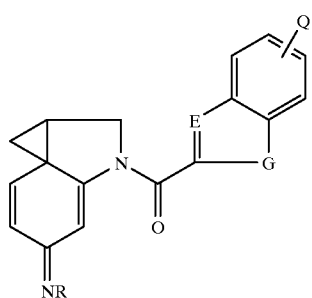

(III)

where R, E, G and Q are as defined above. The imine group (=NR) may also arise when cleavage of the group P occurs in compounds of the formula (II).

F. Applications of the Invention

The compounds of the invention can be used in a method of treatment of the human or animal body. Such treatment includes a method of treating the growth of neoplastic cells in a patient with neoplastic disease which comprises administering to a patient in need of treatment compounds of formula (I) of the invention, or compounds of formula (II) of the invention as part of an ADEPT or GDEPT therapy system. Neoplastic diseases include leukaemia and solid tumours such as breast, bowel and lung tumours including small cell lung carcinoma.

It will be understood that where treatment of tumours is concerned, treatment includes any measure taken by the physician to alleviate the effect of the tumour on a patient. Thus, although complete remission of the tumour is a desirable goal, effective treatment will also include any measures capable of achieving partial remission of the tumour as well as a slowing down in the rate of growth of a tumour including metastases. Such measures can be effective in prolonging and/or enhancing the quality of life and relieving the symptoms of the disease.

F(i): Compounds of the Formula (I)

Compounds of the formula (I) of the present invention may be used in a method of treatment of neoplastic disease in a patient, which method comprises administering to a patient in need of treatment an effective amount of a compound of formula (I). The compound may be administered in the form of a pharmaceutical composition.

While the exact dose of the compound will be at the discretion of the physician, taking account of the condition and needs of the patient, typical doses will be in the range of from about 0.1 to 200 mg/Kg, preferably about from 10 to 100 mg/Kg per patient per day.

F(ii): Adept Therapy

The antibody/enzyme conjugate for ADEPT can be administered simultaneously but it is often found preferable, in clinical practice, to administer the enzyme/agent conjugate before the prodrug, e.g. up to 72 hours or even 1 week before, in order to give the enzyme/agent conjugate an opportunity to localise in the region of the tumour target. By operating in this way, when the prodrug is administered, conversion of the prodrug to the cytotoxic agent tends to be confined to the regions where the enzyme/agent conjugate is localised, i.e. the region of the target tumour the premature release of the compound of formula (II) is minimised.

In ADEPT the degree of localisation of the enzyme/agent conjugate (in terms of the ratio of localized to freely circulating active conjugate) can be further enhanced using the clearance and/or inactivation systems described in WO89/10140. This involves, usually following administration of the conjugate and before administration of the prodrug, the administration of a component (a "second component") which is able to bind to the such part of the conjugate so as to inactivate the enzyme and/or accelerate the clearance of the conjugate from the blood. Such a component may include an antibody to the enzyme component of the system which is capable of inactivating the enzyme.

The second component may be linked to a macromolecule such as dextran, a liposome, albumin, macroglobulin or a blood group O erythrocyte so that the second component is restrained from leaving the vascular compartment. In addition or as an alternative, the second component may include a sufficient number of covalently bound galactose residues, or residues of other sugars such as lactose or mannose, so that it can bind the conjugate in plasma but be removed together with the conjugate from plasma by receptors for galactose or other sugars in the liver. The second component should be administered and designed for use such that it will not, to any appreciable extent, enter the extravascular space of the tumour where it could inactivate localised conjugate prior to and during administration of the prodrug.

In ADEPT systems, the dose of the prodrug and conjugate will ultimately be at the discretion of the physician, who will take into account such factors as the age, weight and condition of the patient. Suitable doses of prodrug and conjugate are given in Bagshawe et al. Antibody, Immunoconjugates, and Radio-pharmaceuticals (1991), 4, 915–922. A suitable dose of conjugate may be from 500 to 200,000 enzyme units/m$^2$ (e.g. 20,000 enzyme units/m$^2$) and a suitable dose of prodrug may be from about 0.1 to 200 mg/Kg, preferably about from 10 to 100 mg/Kg per patient per day.

In order to secure maximum concentration of the conjugate at the site of desired treatment, it is normally desirable to space apart administration of the two components by at least 4 hours. The exact regime will be influenced by various factors including the nature of the tumour to be targeted and the nature of the prodrug, but usually there will be an adequate concentration of the conjugate at the site of desired treatment within 48 hours.

The ADEPT system when used with nitroreductase also preferably comprises a suitable cofactor for the enzyme. Suitable cofactors include a riboside or ribotide of nicotinic acid or nicotinamide.

The antibody/enzyme conjugate may be administered by any suitable route usually used in ADEPT therapy. This includes parenteral administration of the antibody in a manner and in formulations similar to that described in section F(iv) below.

F(iii): GDEPT Therapy

For use of the vectors in therapy, the vectors will usually be packaged into viral particles and the particles delivered to the site of the tumour, as described in for example Ram et al (ibid). The viral particles may be modified to include an antibody, fragment thereof (including a single chain) or tumour-directed ligand to enhance targeting of the tumour. Alternatively the vectors may be packaged into liposomes. The liposomes may be targeted to a particular tumour. This can be achieved by attaching a tumour-directed antibody to the liposome. Viral particles may also be incorporated into liposomes. The particles may be delivered to the tumour by any suitable means at the disposal of the physician. Preferably, the viral particles will be capable of selectively infecting the tumour cells. By "selectively infecting" it is meant that the viral particles will primarily infect tumour cells and that the proportion of non-tumour cells infected is such that the damage to non-tumour cells by administration of a prodrug will be acceptably low, given the nature of the disease being treated. Ultimately, this will be determined by the physician.

One suitable route of administration is by injection of the particles in a sterile solution. Viruses, for example isolated from packaging cell lines may also be administered by regional perfusion or direct intratumoral direction, or direct injection into a body cavity (intracaviterial administration), for example by intra-peritoneum injection.

The exact dosage regime for GDEPT will, of course, need to be determined by individual clinicians for individual patients and this, in turn, will be controlled by the exact nature of the prodrug and the cytotoxic agent to be released from the prodrug but some general guidance can be given. Chemotherapy of this type will normally involve parenteral administration of modified virus and administration by the intravenous route is frequently found to be the most practical.

In GDEPT systems the amount of virus or other vector delivered will be such as to provide a similar cellular concentration of enzyme as in the ADEPT system mentioned above. Typically, the vector will be administered to the patient and then the uptake of the vector by transfected or infected (in the case of viral vectors) cells monitored, for example by recovery and analysis of a biopsy sample of targeted tissue. This may be determined by clinical trials which involve administering a range of trial doses to a patient and measuring the degree of infection or transfection of a target cell or tumour. The amount of prodrug required will be similar to or greater than that for ADEPT systems.

In using a GDEPT system the prodrug will usually be administered following administration of the vector encoding an enzyme. Suitable doses of prodrug are from about 0.1 to 200 mg/Kg, preferably about from 10 to 100 mg/Kg per patient per day.

F(iv): Administration of Drug or Prodrug

While it is possible for the compounds of formula (I) or the prodrugs of formula (II) to be administered alone it is preferable to present them as pharmaceutical formulations. The formulations comprise the compounds, together with one or more acceptable carriers thereof and optionally other therapeutic ingredients. The carrier or carriers must be "acceptable" in the sense of being compatible with the other ingredients of the formulation and not deleterious to the recipients thereof, for example, liposomes. Suitable liposomes include, for example, those comprising the positively charged lipid (N[1-(2,3-dioleyloxy)propyl]-N,N,N-triethylammonium (DOTMA), those comprising dioleoylphosphatidylethanolamine (DOPE), and those comprising 3β[N-(n',N'-dimethylaminoethane)-carbamoyl] cholesterol (DC-Chol).

Formulations suitable for parenteral or intramuscular administration include aqueous and non-aqueous sterile injection solutions which may contain anti-oxidants, buffers, bacteriostats, bactericidal antibiotics and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose containers, for example sealed ampoules and vials, and may be stored in a freeze-dried (lyophilized) condition requiring only the addition of the sterile liquid carrier, for example water, for injections, immediately prior to use. Injection solutions and suspensions may be prepared extemporaneously from sterile powders, granules and tablets of the kind previously described.

It should be understood that in addition to the ingredients particularly mentioned above the formulations may include other agents conventional in the art having regard to the type of formulation in question. Of the possible formulations, sterile pyrogen-free aqueous and non-aqueous solutions are preferred.

The doses may be administered sequentially, eg. at daily, weekly or monthly intervals, or in response to a specific need of the patient. Preferred routes of administration are oral delivery and injection, typically parenteral or intramuscular injection or intratumoural injection.

The exact dosage regime will, of course, need to be determined by individual clinicians for individual patients and this, in turn, will be controlled by the exact nature of compound of formula (I) but some general guidance can be given. Typical dosage ranges generally will be those described above which may be administered in single or multiple doses. Other doses may be used according to the condition of the patient and other factors at the discretion of the physician.

The following Examples illustrate the invention.

EXAMPLE 1

Preparation of 6-amino-3-(chloromethyl)-1-[5',6',7'-trimethoxyindol-2'-yl)carbonyl]indoline (a) t-Butyl 4-chloro-3-nitrobenzoate A solution of 4-chloro-3-nitrobenzoic acid (10.03 g, 50 mmol), $SOCl_2$ (4.4 mL, 60 mmol) and DMF (4 drops) in 1,2-dichloroethane (150 mL) was stirred under reflux for 14 h, cooled and evaporated. The resulting crude acid chloride was dissolved in THF (100 mL), cooled to 0° C., and a solution of potassium t-butoxide (5.57 g, 50 mmol) in THF (150 mL) was added dropwise over 30 min under nitrogen. The mixture was stirred a further 15 min at 0° C., diluted with aqueous $NaHCO_3$ and extracted with EtOAc (×2), and the extracts were dried ($Na_2SO_4$) and evaporated. Flash chromatography of the residue on silica gel (petroleum ether/EtOAc; 30:1) gave t-butyl 4-chloro-3-nitrobenzoate as a white crystalline solid (11.45 g, 89%), mp (petroleum ether) 70–71° C. $^1H$ NMR ($CDCl_3$) δ8.42 (d, J=2.0 Hz, 1H, H-2), 8.11 (dd, J=8.4, 2.0 Hz, 1H, H-6), 7.61 (d, J=8.4 Hz, 1H, H-5), 1.61 (s, 9H, t-Bu). Anal. Calculated for $C_{11}H_{12}ClNO_4$: 51.3; H, 4.7; N, 5.4; Cl, 13.8. Found: C, 51.6; H, 4.8; N, 5.4; Cl, 14.0%.

(b) Dimethyl (4-carboxy-2-nitrophenyl)malonate

Sodium hydride (13.5 g of a 60% dispersion in oil, 0.34 mol) was washed with petroleum ether (×3) under nitrogen and suspended in dry THF (400 mL). A solution of dimethyl malonate (40.4 mL, 0.35 mol) in THF (50 mL) was added dropwise over 45 min with water-bath cooling, keeping the internal temperature below 30° C., and the resulting gel was broken up with more dry THF (300 mL). The above t-butyl 4-chloro-3-nitrobenzoate (21.7 g, 84 mmol) was added and the mixture was stirred at reflux under nitrogen for 15 h. The red-brown solution was cooled, poured into water, and aqueous HCl (2 N, ca. 60 mL) added slowly until the red nitronate colour was dispersed. The THF was evaporated and the aqueous phase extracted with $CH_2Cl_2$ (×3), the extracts were dried ($Na_2SO_4$) and evaporated. Formic acid (100 mL) was added to the residue and the mixture was stirred at 50° C. for 4 h (when tlc analysis showed no remaining t-butyl ester). The formic acid was evaporated and the residue was taken up in EtOAc and washed with water (×3). The organic layer was extracted with aqueous NaHCO$_3$ (×2), and the aqueous phase was acidified (conc. HCl), and extracted with CH$_2$Cl$_2$ (×2). The organic layer was dried (Na$_2$SO$_4$), evaporated, and the resulting cream solid recrystallized from benzene (ca. 250 mL) to give dimethyl(4-carboxy-2-nitrophenyl)malonate as cream prisms (21.8 g, 87%), mp 147–149° C. $^1$H NMR ((CD$_3$)$_2$SO) δ13.77 (br s, 1H, CO$_2$H), 8.52 (d, J=1.7 Hz, 1H, H-3), 8.28 (dd, J=8.1, 1.7 Hz, 1H, H-5), 7.70 (d, J=8.1 Hz, 1H, H-6), 5.62 (s, 1H, ArCH), 3.71 (s, 6H, CO$_2$Me); $^{13}$C NMR δ166.9, 165.1 (COOMe, COOH), 148.2, 134.0, 133.1, 132.3, 132.1, 125.5 (C-1,2,3,4,5,6), 54.3 (ArCH), 52.9 (OMe). Anal. Calculated for C$_{12}$H$_{11}$NO$_8$: C, 48.5; H, 3.7; N, 4.7. Found: C, 48.7; H, 3.5; N, 4.7%.

(c) Dimethyl [4-(benzyloxycarbonyl)-amino-2-nitrophenyl]malonate

A solution of the above malonate (3.44 g, 11.6 mmol), SOCl$_2$ (1.0 mL, 13.9 mmol) and DMF (4 drops) in 1,2-dichloroethane (60 mL) was stirred under reflux for 1 h, cooled and evaporated. The residue was dissolved in Me$_2$CO (30 mL) and added dropwise over 10 min to a vigorously stirred solution of sodium azide (2.26 g, 35 mmol) in water (30 mL) and acetone (100 ml) at 0° C. After a further 30 min at 0° C., EtOAc (100 mL) was added, most of the Me$_2$CO was evaporated, and the EtOAc layer was washed with water, dried (Na$_2$SO$_4$), and evaporated. The residue was dissolved in dry toluene (35 mL) and stirred at reflux for 40 min. Benzyl alcohol (2.2 mL, 21 mmol) was added to the cooled solution and the mixture stirred at 20° C. for 2 h [until a sample spotted on a tlc plate no longer showed the formation of yellow dimethyl (4-amino-2-nitrophenyl)malonate]. The mixture was then evaporated and the residue was distilled in a Kugelrohr (1 mm Hg, 90° C.) to remove excess benzyl alcohol. Flash chromatography on silica gel, eluting with petroleum ether/EtOAc (3:1) gave dimethyl [4-(benzyloxycarbonyl)-amino-2-nitrophenyl]malonate as a yellow oil (3.77 g, 81%). $^1$H NMR (CDCl3) δ8.16 (d, J=2.3 Hz, 1H, H-3), 7.59 (dd, J=8.5, 2.3 Hz, 1H, H-5), 7.42–7.33 (m, 6H, H-6 and Ph), 7.11 (s, 1H, NH), 5.25 (s, 1H, ArCH), 5.22 (s, 2H, OCH$_2$Ph), 3.78 (s, 6H, CO$_2$Me); $^{13}$C NMR δ167.9, (CO$_2$Me), 152.8 (NCO$_2$), 149.0, 139.1, 135.4, 131.9, 128.7, 128.6, 128.4, 122.7, 121.9, 114.6 (aromatic C), 67.6 (OCH2Ph), 53.5 (ArCH), 53.2 (OMe); MS (DEI) m/z 402 (2%, M$^+$), 91 (100%, C$_7$H$_7$); HRMS calcd. for C$_{19}$H$_{18}$N$_2$O$_8$ 402.10631, found 402.10594.

(d) 2-[4-(Benzyloxycarbonyl)amino-2-nitrophenyl]propane-1,3-diol

A solution of the above 2-nitrophenylmalonate (3.12 g, 7.75 mmol) in THF (80 mL) was added dropwise over 30 min to a solution of diisobutylaluminium hydride (93 mL of a 1M solution in hexanes, 93 mmol) in THF (100 mL) under nitrogen, with cooling in an ice-salt bath (maintaining the internal temperature at −7 to 0° C.). The mixture was allowed to warm to 20° C. over 1 h, then poured into ice-cold aqueous HCl (3 N, 260 mL). The THF was evaporated, the aqueous residue was extracted with EtOAc (×3), and the extracts dried (Na$_2$SO$_4$) and evaporated. Dry column chromatography on silica gel, eluting with EtOAc/petroleum ether (1:3 then 1:1 then 2:1) gave recovered dimethyl [4-(benzyloxycarbonyl)amino-2-nitrophenyl]-malonate (0.42 g, 13%) and 2-[4-(benzyloxycarbonyl)amino-2-nitrophenyl]propane-1,3-diol as a light brown foam (1.35 g, 50%). A sample of the latter was crystallized from CHCl$_3$, giving pale yellow flakes, mp 119–121° C. $^1$H NMR ((CD$_3$)$_2$SO) δ10.15 (s, 1H, NH), 7.97 (d, J=2.2 Hz, 1H, H-3), 7.60 (dd, J=8.6, 2.2 Hz, 1H, H-5), 7.49 (d, J=8.6 Hz, 1H, H-6), 7.45–7.33 (m, 5H, Ph), 5.18 (s, 2H, OCH2Ph), 4.67 (t, J=5.3 Hz, 2H, OH), 3.73–3.66 (m, 2H, CHHOH), 3.63–3.56 (m, 2H, CHHOH), 3.23 (p, J=6.4 Hz, 1H, ArCH); $^{13}$C NMR δ153.3 (NCO$_2$), 150.9, 137.8, 136.2, 129.0 (C-1, 2,4 and i C of Ph), 129.9, 121.7, 112.3 (C-3,5,6), 128.4, 128.11, 128.09, (o, m, p C of Ph), 66.1 (OCH$_2$Ph), 61.8 (CH$_2$OH), 44.1 (ArCH). Anal. Calculated for C$_{17}$H$_{18}$N2O$_6$: C, 59.0; H, 5.2; N, 8.1. Found: C, 58.9; H, 5.4; N, 8.3%.

(e) 2-[2-Amino-4-(benzyloxycarbonyl)aminophenyl]propane-1,3-diol

A solution of the above nitrodiol (1.02 g, 2.9 mmol) in EtOH (80 mL) with PtO$_2$ (0.12 g) was hydrogenated at 50 psi and 20° C. for 50 min, filtered through Celite, and evaporated. Dry column chromatography on silica gel, eluting with EtOAc/MeOH (20:1 then 10:1) gave the title compound as a very pale yellow oil (0.88 g, 94%). $^1$H NMR ((CD$_3$)$_2$SO) δ9.36 (s, 1H, NH), 7.43–7.30 (m, 5H, Ph), 6.82 (d, J=2 Hz, 1H, H-3), 6.81 (d, J=8.3 Hz, 1H, H-6), 6.58 (dd, J=8.3, 2.1 Hz, 1H, H-5), 5.12 (s, 2H, OCH$_2$Ph), 4.82 (s, 2H, NH$_2$ or OH), 4.50 (s, 2H, NH$_2$ or OH), 3.69–3.62 (m, 2H, CHHOH), 3.54–3.46 (m, 2H, CHHOH), 2.83 (p, J=6.2 Hz, 1H, ArCH); $^{13}$C NMR δ153.2 (NCO$_2$), 146.8, 137.2, 136.8, 120.4 (C-1,2,4 and i C of Ph), 128.3, 127.92, 127.86 (o, m, p C of Ph), 127.0, 107.2, 105.2 (C-3,5,6), 65.3 (OCH$_2$Ph), 62.3 (CH$_2$OH), 43.2 (ArCH); MS (DEI) m/z 316 (30%, M$^+$), 285 (30%, M—CH$_2$OH), 91 (100%, C$_7$H$_7$); HRMS calcd. for C$_{17}$H$_{20}$N$_2$O$_4$ 316.14231, found 316.14182.

(f) 2-[4-(Benzyloxycarbonyl)amino-2-(t-butyloxvcarbonyl)aminophenyl]propane-1,3-diol A solution of the above aminodiol (0.70 g, 2.21 mmol), di-t-butyldicarbonate (0.53 g, 2.4 mmol) and Na$_2$CO$_3$ (0.26 g, 2.4 mmol) in THF (120 mL) and water (60 mL) was stirred at 20° C. More di-t-butyldicarbonate (2×0.53 g) was added after 5 and 8 days, with sufficient THF and water to maintain a single phase. After 14 days the THF was evaporated, the aqueous layer extracted with EtOAc (×2), and the organic extracts dried (Na$_2$SO$_4$) and evaporated. Dry column chromatography on silica gel, eluting with EtOAc/petroleum ether (2:1 then 4:1) gave the title compound as a white foam (0.78 g, 85%). $^1$H NMR [(CD3)2SO] δ9.67 (s, 1H, NH), 8.62 (s, 1H, NH), 7.60 (s, 1H, H-3), 7.44–7.31 (m, 5H, Ph), 7.19 (dd, J=8.5, 1.7 Hz, 1H, H-5), 7.08 (d, J=8.5 Hz, 1H, H-6), 5.14 (s, 2H, OCH2Ph), 4.84 (t, J=4.7 Hz, 2H, OH), 3.78–3.70 (m, 2H, CHHOH), 3.54–3.45 (m, 2H, CHHOH), 2.98 (p, J=6.3 Hz, 1H, ArCH), 1.45 (s, 9H, t-Bu). 13C NMR d 153.3 (resolves into two peaks on D$_2$O exchange, 2×NCO$_2$), 137.1, 137.0, 136.7, 129.4 (C-1,2,4 and i C of Ph), 128.4, 127.91, 127.87 (o, m, p C of Ph), 127.4, 114.6, 114.4 (C-3,5,6), 78.8 (OCMe$_3$), 65.5 (OCH$_2$Ph), 62.8 (CH$_2$OH), 43.9 (ArCH), 28.1 (C(CH3)3); MS (DEI) m/z 416 (2%, M$^+$), 91 (100%, C$_7$H$_7$); HRMS calcd. for C$_{22}$H$_{28}$N$_2$O$_6$ 416.19474, found 416.19544.

(g) 6-[(Benzyloxycarbonyl)amino]-1-(t-butyloxycarbonyl)-3-(hydroxymethyl)indoline Diethylazodicarboxylate (0.47 mL, 3.0 mmol) was added dropwise over 5 min to a solution of the above t-butyloxycarbonyl diol (0.74 g, 1.78 mmol) and triphenylphosphine (0.84 g, 3.2 mmol) in THF (60 mL) under nitrogen and the mixture stirred at 20° C. After 10 min the mixture was diluted with EtOAc, washed with aqueous NaCl, and the organic phase dried (Na$_2$SO$_4$) and evaporated. Dry column chromatography on silica gel, eluting with EtOAc/petroleum ether (1:2) gave an overlapping band of reduced diethylazodicarboxylate and title product. A small fraction of the product was obtained in a pure state as a very pale yellow oil. $^1$H NMR ((CD$_3$)$_2$SO) δ9.68 (s, 1H, NH), 7.97 (br s, 1H, H-7), 7.44–7.31 (m, 5H, Ph), 7.11 (d, J=8.1

Hz, 1H, H-4), 6.98 (br d, J=8 Hz, 1H, H-5), 5.13 (s, 2H, OCH$_2$Ph), 4.90 (t, J=5.0 Hz, 1H, OH), 3.94 (apparent t, J=10.3 Hz, 1H, NCHH), 3.75 (dd, J=11.3, 5.1 Hz, 1H, NCHH), 3.61–3.54 (m, collapses to dd, J=10.2, 4.7 Hz in D2O exchange, 1H, CHHOH), 3.41–3.28 (m, 2H, ArCHCHHOH), 1.51 (s, 9H, t-Bu); $^{13}$C NMR δ153.2, 151.6 (2×NCO$_2$), 143 (br), 138.6, 136.7, 126.4 (C-6,8,9 and i C of Ph), 128.3, 127.96, 127.90 (o, m, p C of Ph), 124.4, 112.1, 105.0 (C-4,5,7), 79.7 (OCMe$_3$), 65.5, 63.9 (OCH$_2$Ph, CH$_2$OH), 51.4 (C-2), 41.2 (C-3), 28.0 (C(CH$_3$)$_3$); MS (DEI) m/z 398 (4%, M+); HRMS calcd. for C$_{22}$H$_{26}$N$_2$O$_5$ 398.18417, found 398.18402.

(h) 6-(Benzyloxycarbonyl)amino]-1-(t-butyloxycarbonyl)-3-[(methanesulfonyloxy)methyl]indoline Methanesulfonyl chloride (0.25 mL, 3.2 mmol) was added to a solution of the mixture obtained from the previous reaction (ca. 1.8 mmol of alcohol) and Et$_3$N (0.50 mL, 3.6 mmol) in CH$_2$Cl$_2$ (60 mL) at 0° C., and the mixture was stirred for 15 min. Aqueous NaHCO$_3$ was added, the mixture was extracted with CH$_2$Cl$_2$ (×2) and the extracts dried (Na$_2$SO$_4$) and evaporated. Flash chromatography on silica gel, eluting with CHCl$_3$.EtOAc (20:1 then 10:1) gave title compound as a white foam (0.79 g, 93% for two steps). 1H NMR (CDCl$_3$) δ7.73 (s, 1H, H-7), 7.41–7.31 (m, 5H, Ph), 7.12 (d, J=8.1 Hz, 1H, H-4), 6.73 (s, 1H, H-5), 5.19 (s, 2H, OCH$_2$Ph), 4.32 (dd,. J=9.9, 5.5 Hz, 1H, CHHOSO$_2$Me), 4.18 (dd, J=9.9, 8.1 Hz, 1H, CHHOSO$_2$Me), 4.11–4.02 (m, 1H, NCHH), 3.92–3.84 (m, 1H, NCHH), 3.72–3.62 (m, 1H, H-3), 2.96 (s, 3H, OSO$_2$Me), 1.56 (s, 9H, t-Bu); $^{13}$C NMR δ153.2, 152.1 (2×NCO$_2$), 143.9, 138.7, 136.0, 123.6 (C-6, 8,9 and i C of Ph), 128.6, 128.3 (br) (o, m, p C of Ph), 124.9, 112.7, 105.9 (C-4,5,7), 81.2 (OCMe$_3$), 71.0 (CH$_2$OSO$_2$), 67.0 (OCH$_2$Ph), 51.1 (C-2), 39.1 (C-3), 37.5 (OSO$_2$CH$_3$), 28.4 (C(CH$_3$)$_3$); MS (DEI) m/z 476 (5%, M+), 91 (100%, C7H7) ; HRMS calcd. for C$_{23}$H$_{28}$N$_2$O$_7$S 476.16172, found 476.16070.

(i) 6-[(Benzyloxycarbonyl)amino]-3-[(methanesulfonyloxy)methyl]-1-[(5',6',7'-trimethoxyindol-2'-yl)carbonyl]indoline The above benzyloxycarbonylaminoindoline (306 mg, 0.64 mmol) was stirred in HCl-saturated EtOAc (10 mL) at 20° C. for 1 h (until tlc indicated complete reaction) and the mixture was evaporated. 1-(3-Dimethylaminopropyl)-3-ethylcarbodiimide hydrochloride (EDCI, 0.37 g, 1.9 mmol) and 5,6,7-trimethoxyindole-2-carboxylic acid [Y. Fukuda et al, Tetrahedron, 1994, 50, 2793–2808] (161 mg, 0.64 mmol) in DMF (15 mL) were added to the crude indoline hydrochloride, and the mixture stirred at 20° C. under nitrogen for 22 h. The DMF was evaporated, the residue was dissolved in EtOAc and water, extracted once more with EtOAc, and the organic extracts were dried (Na$_2$SO$_4$) and evaporated. Dry column chromatography of the residue on silica gel, eluting with EtOAc/petroleum ether (1:1), gave title compound as a pale pink crystalline solid (209 mg, 53%), mp (EtOAc/petroleum ether) 153–154° C. $^1$H NMR δ11.44 (s, 1H, indole NH), 9.85 (s, 1H, carbamate NH), 8.38 (s, 1H, H-7), 7.46–7.33 (m, 5H, Ph), 7.33 (d, J=8.2 Hz, 1H, H-4), 7.25 (dd, J=8.2, 1.8 Hz, 1H, H-5), 7.03 (d, J=1.9 Hz, 1H, H-3'), 6.95 (s, 1H, H-4'), 5.15 (s, 2H, OCH$_2$Ph), 4.62 (apparent t, J=10 Hz, 1H, CH$_2$), 4.45 (dd, J=9.8, 5.1 Hz, 1H, CH$_2$), 4.35 (dd, J=9.8, 7.2 Hz, 1H, CH$_2$), 4.27 (dd, J=10.9, 5.3 Hz, 1H, CH$_2$), 3.93 (s, 3H, OCH$_3$), 3.87–3.80 (m, 1H, H-3), 3.81 (s, 3H, OCH$_3$), 3.80 (s, 3H, OCH$_3$), 3.18 (s, 3H, OSO$_2$Me). $^{13}$C NMR δ160.1, 153.3, 149.1, 144.0, 139.8, 139.1, 139.0, 136.6, 130.8, 124.6, 123.1 (C-6,8,9,2',5',6',7', 8',9', i C of Ph, NCO, NCO$_2$, one peak not observed), 128.4, 128.0, 127.9 (o, m, p C of Ph), 125.3, 113.9, 107.7, 106.1, 98.0 (C-4,5,7,3',4'), 71.3 (CH$_2$OSO$_2$), 65.6 (OCH$_2$Ph), 61.0, 60.9, 55.9 (3×OCH$_3$), 53.0 (C-2), 39.3 (C-3), 36.5 (OSO$_2$CH$_3$). Anal. Calculated for C$_{30}$H$_{31}$N$_3$O$_9$S.0.5EtOAc: C, 58.8; H, 5.4; N, 6.4. Found: C, 58.7; H, 5.3; N, 6.6%.

(j) 6-Amino-3-(chloromethyl)-1-[(5',6',7'-trimethoxyindol-2'-yl)carbonyl]indoline A solution of ammonium formate (0.24 g, 3.8 mmol) in water (12 mL) was added to the above indoline (233 mg, 0.38 mmol) and Pd/C (5%, 100 mg) in THP (50 mL) and the mixture was stirred at 20° C. More Pd/C (30 mg) was added after 70 min, and after 100 min (tlc indicates complete reaction) the catalyst was filtered off and washed with EtOAc. The filtrate was diluted with aq. NaCl, extracted with EtOAc (×2), and the extracts dried (Na$_2$SO$_4$) and evaporated. Dry column chromatography (eluting with 2:1 EtOAc:petroleum ether) gave 6-amino-3-[(methanesulfonyloxy)methyl]-1-[(5',6',7'-trimethoxyindol-2'-yl)carbonyl]indoline as a pale yellow foam (154 mg, 85%). This mesylate (150 mg, 0.32 mmol) and LiCl (0.13 g, 3.2 mmol) were stirred in DMF (5 mL) at 70° C. under nitrogen for 80 min, and the DMF evaporated. The residue was dissolved in EtOAc and water, extracted once more with EtOAc, and the organic extracts dried (Na$_2$SO$_4$) and evaporated. Dry column chromatography, eluting with EtOAc/petroleum ether (1:1) gave the title compound of the invention (87 mg, 66%), mp (EtOAc/Et$_2$O) 173–174° C. $^1$H NMR [(CD$_3$)$_2$SO] δ11.36 (d, J=1.6 Hz, 1H, NH), 7.44 (br s, 1H, H-7), 7.05 (d, J=8.0 Hz, 1H, H-4), 6.96 (d, J=2.1 Hz, 1H, H-3'), 6.95 (s, 1H, H-4'), 6.30 (dd, J=8.0, 2.2 Hz, 1H, H-5), 5.18 (s, 2H, NH$_2$), 4.54 (dd, J=10.8, 8.7 Hz, 1H, NCHH), 4.20 (dd, J=10.8, 4.4 Hz, 1H, NCHH), 3.93 (s, 3H, OCH$_3$), 3.91 (dd, J=9.9, 3.5 Hz, 1H, CHHCl), 3.81 (s, 3H, OCH$_3$), 3.79 (s, 3H, OCH$_3$), 3.74–3.60 (m, 2H, CHCHHCl). $^{13}$C NMR δ159.9, 149.0, 144.2, 139.6, 139.0, 131.2, 125.1, 123.1, 118.8 (C-6,8,9,2',5',6',7',8',9', NCO, one peak not observed), 124.7, 109.5, 105.6, 102.9, 98.0 (C-4,5,7,3',4'), 61.0, 60.9, 55.9 (3×OCH$_3$), 54.5 (C-2), 47.9 (CH$_2$Cl), 41.8 (C-3). Anal. Calculated for C$_{21}$H$_{22}$ClN$_3$O$_4$: C, 60.7; H, 5.3; N, 10.1. Found: C, 60.7; H, 5.4; N, 9.8%.

EXAMPLE 2

Alternative Synthesis of 6-amino-3-(chloromethyl)-1-[(5',6',7'-trimethoxyindol-2'-yl)carbonyl]indoline This example illustrates the route of synthesis outlined in Scheme 2.

(a) t-Butyl 2-chloro-5-nitrobenzoate

A solution of 2-chloro-5-nitrobenzoic acid (10.14 g, 50.3 mmol), thionyl chloride (4.4 mL, 60 mmol) and DMF (4 drops) in 1,2-dichloroethane (150 mL) was stirred at reflux for 14 h, cooled and evaporated. The acid chloride was dissolved in THF (100 mL), cooled to 0° C., and a solution of potassium t-butoxide (5.57 g, 50 mmol) in THF (150 mL) added dropwise over 30 min under nitrogen. The mixture was stirred a further 15 min at 0° C., diluted with aq. NaHCO$_3$, extracted with EtOAc (×2), and the extracts dried (Na$_2$SO$_4$) and evaporated. Crystallisation from petroleum ether gave t-butyl 2-chloro-5-nitrobenzoate as a white crystalline solid (10.1 g, 78%), mp 91.5–92° C. $^1$H NMR (CDCl$_3$) δ8.59 (d, J=2.8 Hz, 1H, H-6), 8.24 (dd, J=8.8, 2.8 Hz, 1H, H-4), 7.63 (d, J=8.8 Hz, 1H, H-3), 1.65 (s, 9H, t-Bu); 13C NMR (CDCl$_3$) d 163.0 (CO2tBu), 146.1, 140.0, 133.3, (C-1,2,5), 132.0, 126.1, 126.0 (C-3,4,6), 84.0 (CMe3), 28.1 (CH$_3$). Anal. Calculated for C$_{11}$H$_{12}$ClNO$_4$: C, 51.3; H, 4.7; N, 5.4; Cl, 13.8. Found: C, 51.3; H, 4.5; N, 5.6; Cl, 14.0%.

(b) Dimethyl (2-carboxy-4-nitrophenyl)malonate

Sodium hydride (12.42 g of a 60% dispersion in oil, 310 mmol) was washed with petroleum ether (×3) under nitrogen and suspended in dry DMSO (250 mL). A solution of dimethyl malonate (37.3 mL, 330 mmol) in DMSO (50 mL) was added dropwise over 35 min with water-bath cooling. t-Butyl 2-chloro-5-nitrobenzoate (20.0 g, 78 mmol) was added and the mixture stirred at 70–80° C. under nitrogen for 4 h. The red-brown solution was cooled, poured into water (300 mL), and aq. HCl (2 N, 60 mL) added slowly until the red nitronate colour was dispersed. The mixture was extracted with $CH_2Cl_2$ (×3), the extracts were dried ($Na_2SO_4$) and evaporated. Formic acid (60 mL) was added to the residue and the mixture stirred at 20° C. for 15 h then 50° C. for 7 h (when tlc analysis showed no remaining t-butyl ester). The formic acid was evaporated and the residue taken up in EtOAc and washed with aq. NaCl (×3). The organic layer was extracted with aq. $NaHCO_3$ (×3), the aqueous phase acidified (c.HCl), and extracted with $CH_2Cl_2$ (×3). The organic phase was dried ($Na_2SO_4$), evaporated, and the residue recrystallised from benzene (two crops) to give dimethyl (2-carboxy-4-nitrophenyl)malonate as cream needles (20.27 g, 88%), mp 163–164° C. $^1$H NMR ($CDCl_3$) δ8.99 (d, J=2.5 Hz, 1H, H-3), 8.44 (dd, J=8.6, 2.5 Hz, 1H, H-5), 8.4 (v br s, 1H, $CO_2H$), 7.73 (d, J=8.6 Hz, 1H, H-6), 5.94 (s, 1H, ArCH), 3.83 (s, 6H, $CO_2Me$); 13C NMR δ169.6, 167.8 ($CO_2Me$, $CO_2H$), 147.4, 141.4, 132.2, 129.7, 127.6, 126.8 (C-1,2,3,4,5,6), 54.4 (ArCH), 53.3 (OMe). Anal. Calculated for $CH_{11}NO_8$: C, 48.5; H, 3.7; N, 4.7. Found: C, 48.7; H, 3.7; N, 5.0%.

(c) 3,3-Di(methoxycarbonyl)-6-nitro-2-indolone

Triethylamine (8.64 mL, 62 mmol) was added to a solution of dimethyl (2-carboxy-4-nitrophenyl)malonate (18.43 g, 62 mmol) and diphenylphosphoryl azide (DPPA, 13.4 mL, 62 mmol) and the mixture stirred at reflux for 15 h. The orange-brown solution was cooled, concentrated to a small volume, and the solid filtered off, washing with 2N HCl then water. The solid was triturated with hot MeOH (ca. 80 mL) to give title compound as a pale yellow powder (15.4 g, 84%), mp 234–239° C. (dec.). $^1$H NMR (($CD_3$)$_2$SO) δ11.43 (br s, 1H, NH), 7.97 (dd, J=8.3, 2.1 Hz, 1H, H-5), 7.66 (d, J=8.3 Hz, 1H, H-4), 7.62 (d, J=2.1 Hz, 1H, H-7), 3.76 (s, 6H, $CO2Me$); 13C NMR δ167.4, 163.9 (CO2Me, CONH), 148.4, 143.7, 130.4 (C-6,8,9), 126.7, 117.7, 104.6 (C-4,5,7), 65.7 (C-3), 54.0 (OMe); IR (KBr) 1767 (CONH), 1736 ($CO_2Me$), 1524 ($NO_2$), 1348 ($NO_2$), 1246 cm-1; MS (DEI) 294 (85%, $M^+$), 250 (100%, M—$CO_2$); HRMS calcd. for $C_{12}H_{10}N_2O_7$ 294.04880, found 294.04851. Anal. Calculated for $C_{12}H_{10}N_2O$: C, 49.0; H, 3.4; N, 9.5. Found: C, 49.1; H, 3.4; N, 9.6%.

(d) 3,3-Di(methoxycarbonyl)-6-nitroindoline

Borane-dimethylsulfide (6.35 mL, 63 mmol) was added to a suspension of 3,3-di(methoxycarbonyl)-6-nitro-2-indolone (10.38 g, 35.2 mmol) in THF (350 mL) under nitrogen, and the mixture stirred at reflux for 1 h. The pale yellow solution was cooled, MeOH (10 mL), then $H_2O$ (10 mL), then aq. HCl (2 N, 50 mL) added, and the mixture stirred at 20° C. for a few minutes. The THF was evaporated and the aqueous residue extracted with EtOAc (×2). The extracts were dried ($Na_2SO_4$) and evaporated, and the resulting orange solid triturated with $CH_2Cl_2$ (2×100 mL) at 20° C. and filtered to remove most of the 3-(methoxycarbonyl)-6-nitroindole impurity. The $CH_2Cl_2$ solution was filtered through a short column of silica, eluting with more $CH_2Cl_2$, the solvent evaporated, and the resulting yellow solid recrystallised from MeOH to give title compound as a yellow crystalline solid (5.11 g, 52%), mp 139.5–140.5° C. $^1$H NMR ($CDCl_3$) δ7.64 (dd, J=8.3, 2.1 Hz, 1H, H-5), 7.56 (d, J=8.3 Hz, 1H, H-4), 7.41 (d, J=2.1 Hz, 1H, H-7), 4.24 (d, J=1.9 Hz, 2H, $NHCH_2$), 4.16 (br s, 1H, NH), 3.82 (s, 6H, $CO_2Me$); $^{13}$C NMR δ168.7 ($CO_2Me$), 151.7, 149.8, 130.8 (C-6,8,9), 127.2, 114.2, 104.2 (C-4,5,7), 62.7 (C-3), 54.1 (C-2), 53.6 (OMe); IR (KBr) 3351 (NH), 1732 ($CO_2Me$), 1535 ($NO_2$), 1351 ($NO_2$), 1279 cm-1. Anal. Calculated for $C_{12}H_{12}N_2O_6$: C, 51.4; H, 4.3; N, 10.0. Found: C, 51.4; H, 4.4; N, 10.0%.

(e) 1-(t-Butyloxycarbonyl)-3,3-di(methoxycarbonyl)-6-nitroindoline

A solution of 3,3-di(methoxycarbonyl)-6-nitroindoline (3.04 g, 10.8 mmol), di-t-butyldicarbonate (3.55 g, 16.3 mmol) and 4-dimethylaminopyridine (70 mg, 0.5 mmol) in THF (100 mL) was stirred at 20° C. for 2 h then at reflux for 10 min (until tlc analysis showed complete conversion). The THF was evaporated and the residue purified by dry column chromatography, eluting with EtOAc/petroleum ether (1:4), to give title compound as a pale yellow foam (4.10 g, 99%). A sample was crystallised from MeOH, giving very pale yellow needles, mp 131.5–132.5° C. $^1$H NMR ($CDCl_3$) δ8.70, 8.34 (2 x br s, 1H, H-7), 7.89 (dd, J=8.5, 2.2 Hz, 1H, H-5), 7.66 (d, J=8.5 Hz, 1H, H-4), 4.59 (s, 2H, $NCH_2$), 3.83 (s, 6H, $CO_2Me$), 1.60 (s, 9H, t-Bu); 13C NMR δ168.1 ($CO_2Me$), 151.2, 149.7 (C-6,8,9, $NCO_2$, two peaks not observed), 127.4, 117.6, 110.0 (C-4,5,7), 82.5 ($OCMe_3$), 61 (br, C-3), 54.6 (C-2), 53.9 (OMe), 28.3 ($C(CH_3)_3$). Anal. Calculated for $C_{17}H_{20}N_2O_8$: C, 53.7; H, 5.3; N, 7.4. Found: C, 53.6; H, 5.4; N, 7.5%.

(f) 1-(t-Butyloxycarbonyl)-3-(methoxycarbonyl)-6-nitroindoline

NaOMe (4.8 mL of a 1.28 M solution in MeOH, 6.1 mmol) was added dropwise to a solution of 1-(t-butyloxycarbonyl)-3,3-di(methoxycarbonyl)-6-nitroindoline (2.11 g, 5.55 mmol) in THF (100 mL) under nitrogen at 20° C., immediately giving an intense purple colour. After 5 min trifluoroacetic acid (0.51 mL, 6.7 mmol) was added in one portion, causing the nitronate colour to disperse. The pale yellow solution was diluted with aq. NaCl, extracted with EtOAc, and the extracts dried ($Na_2SO_4$) and evaporated to give crude title compound as a pale yellow oil. This compound showed signs of air oxidation on standing at room temperature, so was not further purified but used directly in the next step. $^1$H NMR ($CDCl_3$) δ8.67, 8.34 (2 x br s, 1H, H-7), 7.85 (dd, J=8.2, 2.1 Hz, 1H, H-5), 7.49 (d, J=8.2 Hz, 1H, H-4), 4.48 (dd, J=10.5, 5.4 Hz, 1H, $NCH_2CH$), 4.28 (dd, J=10.5, 5.3 Hz, 1H, $NCH_2CH$), 4.22 (t, J=10.6 Hz, 1H, $NCH_2CH$), 3.82 (s, 3H, $CO_2Me$), 1.60 (s, 9H, t-Bu): 13C NMR δ170.5 ($CO_2Me$), 151.6, 149.1 (C-6,8,9, $NCO_2$, two peaks not observed), 125.5, 117.7, 109.9 (C-4,5,7), ($OCMe_3$ peak not observed), 53.1 (OMe), 50.3 (C-2), 44.4 (C-3), 28.3 ($C(CH_3)_3$). HRMS calculated for $C_{15}H_{18}N_2O_6$: 322.11649. Found: 322.11627.

(g) 1-(t-Butyloxycarbonyl)-3-(hydroxymethyl)-6-nitroindoline

The crude monoester from the above procedure was dissolved in THF (80 mL) and added dropwise over 30 min to a solution of diisobutylaluminium hydride (22.2 mL of a 1 M solution in toluene, 22.2 mmol) in THF (100 mL) under nitrogen at 0° C. The yellow-orange solution was stirred at this temperature for 25 min, then poured into ice-cold aqueous HCl (2 N, 100 mL) and extracted with EtOAc (×2). The extracts were dried ($Na_2SO_4$), evaporated, and the residue purified by dry column chromatography, eluting with EtOAc/petroleum ether (1:1) to give as a yellow-orange solid (1.30 g, 80% from the diester). A sample was recrystallised from benzene, giving a yellow crystalline solid, mp 168.5–169° C. $^1$H NMR ($CDCl_3$) δ8.64, 8.31 (2 x br s, 1H, H-7), 7.83 (dd, J=8.2, 2.3 Hz, 1H, H-5), 7.34 (d, J=8.2 Hz, 1H, H-4), 4.16 (dd, J=11.4, 10.3 Hz, 1H, H-2), 3.96 (dd, J=11.4, 5.4 Hz, 1H, H-2), 3.84 (d, J=6.2 Hz, 2H, CH$_2$OH), 3.62–3.54 (m, 1H, H-3), 1.91 (br s, 1H, OH), 1.59 (s, 9H, t-Bu); 13C NMR δ152.0, 148.6, 144 (br), 139 (br) (C-6,8,9, NCO$_2$), 124.6, 117.7, 109.7 (C-4,5,7), 82 (br, OCMe$_3$), 64.8 (CH$_2$OH), 51.3 (C-2), 41.8 (C-3), 28.3 (C(CH$_3$)$_3$). Anal. Calculated for C$_{14}$H$_{18}$N$_2$O$_5$: C, 57.1; H, 6.2; N, 9.5. Found: C, 57.2; H, 6.2; N, 9.5%.

(h) 1-(t-Butyloxycarbonyl)-3-(chloromethyl)-6-nitroindoline

Methanesulfonyl chloride (0.57 mL, 7.4 mmol) was added dropwise to a solution of 1-(t-butyloxycarbonyl)-3-(hydroxymethyl)-6-nitroindoline (1.21 g, 4.11 mmol) and Et$_3$N (1.15 mL, 8.2 mmol) in CH$_2$Cl$_2$ (70 mL) at 0° C., and the pale yellow solution stirred for 5 min. Water was added, the mixture was extracted with CH$_2$Cl$_2$ (×2), and the extracts dried (Na$_2$SO$_4$) and evaporated. The crude mesylate was dissolved in DMF (10 mL) with LiCl (0.70 g, 16 mmol) and the mixture stirred at 80° C. under nitrogen for 1 h. The DMF was evaporated, the residue dissolved in EtOAc and water, extracted once more with EtOAc, and the organic extracts dried (Na$_2$SO$_4$) and evaporated. Dry column chromatography, eluting with EtOAc/petroleum ether (1:9), gave title compound as pale yellow foam (1.12 g, 87%). A sample was crystallised from benzene-petroleum ether to give a yellow crystalline solid, mp 111–111.5° C. $^1$H NMR (CDCl$_3$) δ8.67, 8.34 (2 x br s, 1H, H-7), 7.86 (dd, J=8.2, 2.2 Hz, 1H, H-5), 7.35 (d, J=8.2 Hz, 1H, H-4), 4.22 (dd, J=11.6, 9.6 Hz, 1H, H-2), 4.04–3.97 (m, 1H, H-2), 3.82–3.74 (m, 2H, CHHCl, H-3), 3.68–3.62 (m, 1H, CHHCl), 1.60 (s, 9H, t-Bu); $^{13}$C NMR δ151.8, 149.0, 144 (br), 138 (br) (C-6,8,9, NCO$_2$), 124.6, 117.8, 110.0 (C-4,5,7), 82.0 (OCMe$_3$), 52.4 (C-2), 46.3 (CH$_2$Cl), 41.7 (C-3), 28.4 (C(CH$_3$)$_3$). Anal. Calculated for C$_{14}$H$_{18}$ClN$_2$O$_4$: C, 53.8; H, 5.5; N, 11.3; Cl, 11.3. Found: C, 54.0; H, 5.5; N, 9.1; Cl, 11.5%.

(i) 3-(Chloromethyl)-6-nitro-1-[(5',6',7'-trimethoxyindol-2'-yl)carbonyl]indoline 1-(t-Butyloxycarbonyl)-3-(chloromethyl)-6-nitroindoline (134 mg, 0.43 mmol) was stirred in HCl-saturated EtOAc (8 mL) at 20° C. for 2.5 h (until tlc indicated complete reaction) and the mixture evaporated. 1-(3-Dimethylaminopropyl)-3-ethylcarbodiimide hydrochloride (EDCI, 0.25 g, 1.29 mmol) and 5,6,7-trimethoxyindole-2-carboxylic acid (108 mg, 0.43 mmol) in DMF (5 mL) were added, and the mixture stirred at 20° C. Over 10 min the colour faded from-orange to a light yellow-brown solution. After 2 h the DMF was evaporated, the residue dissolved in EtOAc and water, extracted once more with EtOAc, and the organic extracts were dried (Na$_2$SO$_4$) and evaporated. The yellow-orange solid was recrystallised from EtOAc, giving title compound as a yellow crystalline solid (96 mg, 50%), mp 187–188° C. The mother liquors were purified by dry column chromatography, eluting with EtOAc/petroleum ether (1:2), to give a second crop of the product (46 mg, combined yield 74%). $^1$H NMR (CDCl$_3$) δ9.48 (s, 1H, NH), 9.08 (d, J=2.2 Hz, 1H, H-7), 7.92 (dd, J=8.2, 2.2 Hz, 1H, H-5), 7.38 (d, J=8.6 Hz, 1H, H-4), 6.94 (d, J=2.4 Hz, 1H, H-3'), 6.81 (s, 1H, H-4'), 4.73 (dd, J=10.5, 9.6 Hz, 1H, H-2), 4.52 (dd, J=10.5, 5.2 Hz, 1H, H-2), 4.07 (s, 3H, OCH$_3$), 4.02–3.95 (m, 1H, H-3), 3.95 (s, 3H, OCH$_3$), 3.89 (s, 3H, OCH$_3$), 3.87 (dd, J=11.2, 4.7 Hz, 1H, CHHCl), 3.71 (dd, J=11.2, 8.1 Hz, 1H, CHHCl); $^{13}$C NMR δ160.4 (NCO), 150.3, 148.7, 144.7, 140.7, 138.8, 137.7, 128.8, 125.8, 123.5 (C-6,8,9, 2',5',6',7', 8',9'), 124.2, 119.5, 112.9, 106.9, 97.5 (C-4,5,7, 3',4'), 61.4, 61.1, 56.2 (3×OCH3), 54.3 (C-2), 46.1 (CH$_2$Cl), 43.2 (C-3). Anal. Calculated for C$_{21}$H$_{20}$ClN$_3$O$_6$: C, 56.6; H, 4.5; N, 9.4; Cl, 8.0. Found: C, 54.8; H, 4.5; N, 9.3; Cl, 8.1%.

(j) 6-Amino-3-(chloromethyl)-1-[(5',6',7'-trimethoxyindol-2'-yl)carbonyl]indoline A solution of 3-(chloromethyl)-6-nitro-1-[(5',6',7-trimethoxyindol-2'-yl)carbonyl]indoline (57 mg, 0.13 mmol) in THF (8 mL) with PtO$_2$ (25 mg) was hydrogenated at 45 psi and 20° C. for 20 min, filtered through Celite, and evaporated. Dry column chromatography, eluting with EtOAc/petroleum ether (1:1), gave title compound of the invention (53 mg, 100%), identical (tlc, $^1$H NMR) to the material prepared in Example 1 above.

EXAMPLE 3

3-(Chloromethyl)-6-[(4"-nitrobenzyloxycarbonyl) amino]-1-[(5',6',7'-trimethoxyindol-2'-yl)carbonyl] indoline 4-Nitrobenzyl chloroformate (27 mg, 1.7 mmol) was added to a solution of 1 (30 mg, 0.07 mmol) in THF (4 mL) at 0° C., and the mixture was stirred at this temperature for 30 min. Water was added, the mixture was extracted with EtOAc (×2), and the extracts dried (Na$_2$SO$_4$) and evaporated. Flash chromatography, eluting with EtOAc/petroleum ether (1:1) gave title compound (33 mg, 77%) as a pale yellow powder, mp (trituration with Et2O from CHCl$_3$) 199–200° C.). $^1$H NMR [(CD3)2SO] δ11.43 (s, 1H, indole NH), 9.97 (s, 1H, carbamate NH), 8.35 (br s, 1H, H-7), 8.28 (br d, J=8.8 Hz, 2H, H-3",5"), 7.70 (br d, J=8.8 Hz, 2H, H-2",6"), 7.34 (d, J=8.2 Hz, 1H, H-4), 7.24 (dd, J=8.2, 1.8 Hz, 1H, H-5), 7.02 (d, J=2.0 Hz, 1H, H-3'), 6.96 (s, 1H, H-4'); 5.30 (s, 2H, OCH$_2$Ar), 4.63 (dd, J=10.8, 8.7 Hz, 1H, NCHH), 4.28 (dd, J=10.8, 4.5 Hz, 1H, NCHH), 4.02–3.95 (m, 1H, CHHCl), 3.92 (s, 3H, OCH$_3$), 3.86–3.76 (m, 2H, CHCHHCl), 3.81 (s, 3H, OCH$_3$), 3.79 (s, 3H, OCH$_3$). Anal. Calculated for C$_{29}$H$_{27}$ClN$_4$O$_8$): C, 58.5; H, 4.6; N, 9.4. Found: C, 58.4; H, 4.3; N, 13.7%.

EXAMPLE 4

Preparation of 2-[[3-(chloromethyl)-6-nitroindolin-1-yl]carbonyl]-N-[2-(2-pyridinyl)ethyl]indole-6-carboxamide hydrochloride A solution of t-butyl 4-formylbenzoate (8.52 g, 41 mmol) and methyl azidoacetate [M. S. Allen, L. K. Hamaker, A. J. La Loggia, J. M. Cook, Synth. Commun., 1992, 22, 2077–2102] (28.5 g, 248 mmol) in dry MeOH (200 mL) was added dropwise over 1 h to a solution of NaOMe (60 mL of a 3.3M solution in MeOH, 197 mmol) under nitrogen with cooling in an ice-salt bath. The yellow suspension was stirred for a further 1 h at 0° C., allowed to stand at 4° C. for 15 h, then diluted with water and the solid filtered off and dried in the dark. A solution of this crude azidocinnamate (8.76 g, 29 mmol) in dry xylene (400 mL) was added dropwise over 2 h to xylene (100 mL) at ref lux under nitrogen, the solution stirred at reflux for a further 1 h, then cooled and evaporated. Recrystallisation from MeOH gave t-butyl 2-(methoxycarbonyl)indole-6-carboxylate as a white solid (4.72 g, 42%), mp 189–190.5° C. $^1$H NMR [(CD$_3$)$_2$SO] δ12.26 (s, 1H, NH), 8.08 (s, 1H, H-3 or H-7), 7.73 (d, J=8.4 Hz, 1H, H-4), 7.61 (dd, J=8.4, 1.3 Hz, 1H, H-5), 7.21 (d, J=1.3 Hz, 1H, H-3 or H-7), 3.89 (s, 3H, CO$_2$Me), 1.56 (s, 9H, CO$_2$tBu); $^{13}$C NMR δ165.5 (Co$_2$tBu), 161.4 (CO$_2$Me), 136.5, 130.0, 129.9, 127.3 (C-2,6,8,9), 121.9, 120.3, 114.4, 107.5 (C-3,4,5,7), 80.4 (OCMe$_3$), 52.1 (OCH$_3$), 27.8 (tBu). Anal. (C$_{15}$H$_{17}$NO$_4$) C,H,N.

t-Butyl 2-(methoxycarbonyl) indole-6-carboxylate (4.74 g, 17.2 mmol) was stirred in formic acid (35 mL) at 80° C. for 20 min, cooled, diluted with water, and the solid filtered off and dried to give 2-(methoxycarbonyl)indole-6- carboxylic acid (3.78 g, 100%) as a white solid, mp 270.5–271.5° C. $^1$H NMR [(CD$_3$)$_2$SO] δ12.80 (br s, 1H, CO$_2$H), 12.31 (s, 1H, NH), 8.13 (s, 1H, H-3 or H-7), 7.75 (d, J=8.4 Hz, 1H, H-4), 7.66 (dd, J=8.4, 1.4 Hz, 1H, H-5), 7.23 (dd, J=2.0, 0.8 Hz, 1H, H-3 or H-7), 3.91 (s, 3H, CO$_2$Me); $^{13}$C NMR δ167.8 (CO$_2$H), 161.4 (CO$_2$Me), 136.5, 129.8, 129.7, 126.6 (C-2,6,8,9), 121.9, 120.6, 114.7, 107.5 (C-3,4,5,7), 52.0 (OCH$_3$). Anal. (C$_{11}$H$_9$NO$_4$) C,H,N.

A solution of 2-(methoxycarbonyl)indole-6-carboxylic acid (290 mg, 1.32 mmol) and 1,1'-carbonyldiimidazole (257 mg, 1.59 mmol) in THF (20 mL) was stirred at reflux for 1 h then cooled and evaporated. A solution of 2-(2-aminoethyl)pyridine (0.19 mL, 1.6 mmol) in DMF (5 mL) was added and the mixture stirred at 80° C. for 2 h, then cooled and evaporated. Trituration with hot EtOAc gave 2-(methoxycarbonyl)-N-[2-(2-pyridinyl)ethyl]indole-6-carboxamide as a white solid (360 mg, 84%), mp 191–193° C. $^1$H NMR [(CD$_3$)$_2$SO] δ12.24 (s, 1H, indole NH), 8.61 (t, J=5.5 Hz, 1H, amide NH), 8.54–8.50 (m, 1H, H-6'), 7.97 (s, 1H, H-3 or H-7), 7.71 (td, J=7.6, 1.8 Hz, 1H, H-4'), 7.70 (d, J=8.6 Hz, 1H, H-4), 7.55 (dd, J=8.6, 1.4 Hz, 1H, H-5), 7.29 (d, J=7.8 Hz, 1H, H-3'), 7.23 (ddd, J=7.4, 4.8, 0.8 Hz, 1H, H-5'), 7.20 (s, 1H, H-3 or H-7), 3.90 (s, 3H, CO$_2$Me), 3.64 (q, J=6.8 Hz, 2H, NHCH$_2$CH$_2$py), 3.03 (t, J=7.4 Hz, 2H, NHCH$_2$CH$_2$py); $^{13}$C NMR δ166.6 (CONH), 161.5 (CO$_2$Me), 159.2 (C-2'), 136.7, 131.0, 129.1, 128.5 (C-2,6,8,9), 149.0, 136.4, 123.1, 121.6, 121.4, 118.9, 112.2, 107.5 (C-3,4,5,7,3',4',5',6'), 51.9 (OCH$_3$), 39.3, 37.3 (NHCH$_2$CH$_2$py). Anal. (C$_{18}$H$_{17}$N$_3$O$_3$) C,H,N.

A mixture of 2-(methoxycarbonyl)-N-[2-(2-pyridinyl)ethyl]indole-6-carboxamide (326 mg, 1.01 mmol) and KOH (68 mg, 1.21 mmol) in THF (20 mL) and H$_2$O (3 mL) was stirred at 20° C. for 15 h then at 65° C. for 3 h, cooled and neutralised with 2N HCl (0.61 mL, 1.2 mmol). The THF was evaporated, the aqueous residue allowed to cool, and the solid filtered off and dried to give 2-carboxy-N-[2-(2-pyridinyl)ethyl]indole-6-carboxamide as a white solid (258 mg, 83%), mp 198–199° C. $^1$H NMR [(CD$_3$)$_2$SO] δ13.14 (br s, 1H, CO$_2$H), 12.07 (s, 1H, indole NH), 8.59 (t, J=5.6 Hz, 1H, amide NH), 8.54–8.51 (m, 1H, H-6'), 7.95 (s, 1H, H-3 or H-7), 7.71 (td, J=7.7, 1.7 Hz, 1H, H-4'), 7.68 (d, J=8.5 Hz, 1H, H-4), 7.53 (dd, J=8.5, 1.4 Hz, 1H, H-5), 7.29 (d, J=7.8 Hz, 1H, H-3'), 7.23 (ddd, J=7.4, 4.7, 0.8 Hz, 1H, H-5'), 7.13 (d, J=1.2 Hz, 1H, H-3 or H-7), 3.64 (q, J=6.8 Hz, 2H, NHCH$_2$CH$_2$py), 3.02 (t, J=7.4 Hz, 2H, NHCH$_2$CH$_2$py); $^{13}$C NMR δ166.7 (CONH), 162.5 (CO$_2$H), 159.2 (C-2'), 136.5, 130.6, 130.5, 128.7 (C-2,6,8,9), 149.0, 136.4, 123.1, 121.4, 118.7, 112.2, 107.0 (one peak doubled or not observed, C-3,4,5,7,3',4',5',6'), 39.3, 37.3 (NHCH$_2$CH$_2$py). Anal. (C$_{17}$H$_{15}$N$_3$O$_3$) C,H,N.

1-(t-Butoxycarbonyl)-3-(chloromethyl)-6-nitroindoline (248 mg, 0.79 mmol) was stirred in HCl-saturated dioxane (8 mL) at 20° C. for 40 min (until tlc indicated complete reaction) and the mixture evaporated. 1-(3-Dimethylaminopropyl)-3-ethylcarbodiimide hydrochloride (0.30 g, 1.58 mmol) and 2-carboxy-N-[2-(2-pyridinyl)ethyl]indole-6-carboxamide (245 mg, 0.79 mmol) in DMF (20 mL) were added and the orange solution stirred at 20° C. After 24 h the DMF was evaporated, and the residue triturated with EtOAc and aqueous NaHCO$_3$. The solid was filtered off and recrystallised from MeOH to give 2-[[3-(chloromethyl)-6-nitroindolin-1-yl]carbonyl]-N-[2-(2-pyridinyl)ethyl]indole-6-carboxamide as a yellow solid (267 mg, 67%), mp 204–207° C. $^1$H NMR [(CD$_3$)$_2$SO] δ12.15 (s, 1H, indole NH), 8.99 (d, J=2.1 Hz, 1H, H-7), 8.61 (t, J=5.5 Hz, 1H, amide NH), 8.55–8.52 (m, 1H, H-6"), 8.04 (dd, J=8.3, 2.3 Hz, 1H, H-5), 8.02 (s, 1H, H-3' or H-7'), 7.75 (d, J=8.6 Hz, 1H, H-4 or H-4'), 7.74 (d, J=8.3 Hz, 1H, H-4 or H-4'), 7.71 (dd, J=7.6, 1.9 Hz, 1H, H-4"), 7.56 (dd, J=8.5, 1.3 Hz, 1H, H-5'), 7.31 (d, J=7.7 Hz, 1H, H-3"), 7.28 (d, J=1.4 Hz, 1H, H-3' or H-7'), 7.23 (ddd, J=7.2, 4.9, 0.8 Hz, 1H, H-5"), 4.86 (t, J=10.1 Hz, 1H, H-2), 4.51 (dd, J=10.7, 5.1 Hz, 1H, H-2), 4.19–4.06 (m, 3H, H-3 and CH$_2$Cl), 3.66 (q, J=6.7 Hz, 2H, NHCH$_2$CH$_2$py), 3.04 (t, J=7.4 Hz, 2H, NHCH$_2$CH$_2$py); $^{13}$C NMR δ166.7 (CONH), 160.4 (CON), 159.2 (C-2"), 147.6, 144.6, 139.9, 135.7, 131.8, 130.8, 128.9 (C-6,8,9,2',6',8',9'), 149.0, 136.4, 123.1, 121.4 (C-3",4",5",6"), 125.5, 121.6, 119.4, 118.8, 112.0, 111.2, 106.1 (C-4,5,7,3',4',5',7'), 54.0 (C-2), 47.0 (CH$_2$Cl), 42.0 (C-3), 39.3, 37.3 (NHCH$_2$CH$_2$py). A sample was converted to the hydrochloride salt and triturated with hot EtOH to give 2-[[3-(chloromethyl)-6-nitroindolin-1-yl) carbonyl]-N-[2-(2-pyridinyl)ethyl]indole-6-carboxamide hydrochloride as a pale yellow powder, mp 250–255° C. (dec.). Anal. (C$_{26}$H$_{22}$ClN$_5$O$_4$.0.25HCl) C,H,N.

EXAMPLE 5

Preparation of 2-[[3-(chloromethyl)-6-nitroindolin-1-yl]carbonyl]-N-[2-(4-morpholinyl)ethyl]indole-6-carboxamide hydrochloride 2-(Methoxycarbonyl)indole-6-carboxylic acid was coupled with 4-(2-aminoethyl)-morpholine by the method described above to give 2-(methoxycarbonyl)-N-[2-(4-morpholinyl)ethyl]indole-6-carboxamide as a white powder (78%), mp 226–227.5° C. (MeOH). $^1$H NMR [(CD$_3$)$_2$SO] δ12.24 (s, 1H, indole NH), 8.42 (t, J=5.6 Hz, 1H, amide NH), 7.97 (s, 1H, H-3 or H-7), 7.71 (d, J=8.4 Hz, 1H, H-4), 7.56 (dd, J=8.4, 1.5 Hz, 1H, H-5), 7.20 (s, 1H, H-3 or H-7), 3.90 (s, 3H, CO$_2$Me), 3.58 (t, J=4.6 Hz, 4H, CH$_2$O), 3.41 (q, J=6.5 Hz, 2H, CONHCH$_2$), 2.48 (t, J=7.0 Hz, 2H, CONHCH$_2$CH$_2$), 2.42 (t, J=4.1 Hz, 4H, NCH$_2$CH$_2$O); $^{13}$C NMR δ166.6 (CONH), 161.5 (CO$_2$Me), 136.7, 131.0, 129.1, 128.5 (C-2,6,8,9), 121.6, 118.9, 112.3, 107.5 (C-3,4,5,7), 66.2 (CH$_2$O), 57.3, 53.2 (CH$_2$N), 51.9 (OCH$_3$), 36.6 (NHCH$_2$). Anal. (C$_{17}$H$_{21}$N$_3$O$_4$) C,H,N.

2-(Methoxycarbonyl)-N-[2-(4-morpholinyl)ethyl]indole-6-carboxamide was hydrolysed by the method described above to give 2-carboxy-N-[2-(4-morpholinyl)ethyl]indole-6-carboxamide as a white solid (83%), mp 227–233° C. $^1$H NMR [(CD$_3$)$_2$SO) δ12.03 (s, 1 H, indole NH), 8.42 (t, J=5.6 Hz, 1H, amide NH), 7.96 (s, 1H, H-3 or H-7), 7.68 (d, J=8.4 Hz, 1H, H-4), 7.54 (dd, J=8.4, 1.3 Hz, 1H, H-5), 7.10 (d J=1.3 Hz, 1H, H-3 or H-7), 3.60 (t, J=4.6 Hz, 4H, CH$_2$O), 3.42 (q, J=6.5 Hz, 2H, CONHCH$_2$), 2.53 (t, J=6.9 Hz, 2H, CONHCH$_2$CH$_2$), 2.50–2.45 (m, 4H, NCH$_2$CH$_2$O); $^{13}$C NMR δ166.8 (CONH), 162.7 (CO$_2$H), 136.5, 131.1, 130.4, 128.7 (C-2,6,8,9), 121.4, 118.6, 112.2, 106.8 (C-3,4,5,7), 66.0 (CH$_2$O), 57.3, 53.1 (CH$_2$N), 36.4 (NHCH$_2$). HRMS (DEI) Calc. for C$_{16}$H$_{19}$N$_3$O$_4$ 317.13756. Found 317.13693.

1-(t-Butoxycarbonyl)-3-(chloromethyl)-6-nitroindoline was coupled with 2-carboxy-N-[2-(4-morpholinyl)ethyl]indole-6-carboxamide by the method described above and triturated with hot MeOH to give 2-[[3-(chloromethyl)-6-nitroindolin-1-yl]carbonyl]-N-[2-(4-morpholinyl)ethyl]indole-6-carboxamide as a yellow solid (50%), mp 227–228° C. (dec.). $^1$H NMR [(CD$_3$)$_2$SO] δ12.15 (s, 1H, indole NH), 8.98 (d, J=2.0 Hz, 1H, H-7), 8.41 (t, J=5.5 Hz, 1H, amide NH), 8.04 (dd, J=8.3, 2.2 Hz, 1H, H-5), 8.01 (s, 1 H, H-3' or H-7'), 7.76 (d, J=8.2 Hz, 1H, H-4 or H-4'), 7.74 (d, J=8.0 Hz, 1H, H-4 or H-4'), 7.57 (dd, J=8.5, 1.1 Hz, 1H, H-5'), 7.28 (d, J=1.4 Hz, 1H, H-3' or H-7'), 4.86 (t, J=10.1 Hz, 1H, H-2), 4.51 (dd, J=10.7, 5.2 Hz, 1H, H-2), 4.19–4.06 (m, 3H, H-3 and CH$_2$Cl), 3.59 (t, J=4.5 Hz, 4H, CH$_2$O), 3.42

(q, J=6.5 Hz, 2H, CONHCH$_2$), 2.50 (t, J=6.9 Hz, 2H, CONHCH$_2$CH$_2$), 2.46–2.41 (m, 4H, NCH$_2$CH$_2$O); $^{13}$C NMR δ166.7 (CONH), 160.4 (CON), 147.6, 144.6, 144.0, 135.7, 131.8, 130.8, 129.0 (C-6,8,9,2',6',8',9'), 125.5, 121.6, 119.5, 118.9, 112.0, 111.2, 106.1 (C-4,5,7,3',4',5',7'), 66.2 (CH$_2$O), 57.4 (CONHCH$_2$CH$_2$), 54.0 (C-2), 53.3 (NCH$_2$CH$_2$O), 47.0 (CH$_2$Cl), 42.0 (C-3), 36.6 (CONHCH$_2$). A sample was converted to the hydrochloride salt and triturated with hot EtOH to give 2-[[3-(chloromethyl)-6-nitroindolin-1-yl]carbonyl]-N-[2-(4-morpholinyl)ethyl] indole-6-carboxamide hydrochloride as a pale yellow powder, mp 280–285° C. (dec.). Anal. (C$_{25}$H$_{26}$ClN$_5$O$_5$.HCl.H$_2$O) C,H,N.

EXAMPLE 6

Preparation of 2-[[3-(chloromethyl)-6-nitroindolin-1-yl]carbonyl]-N-(1,3-dihydroxy-2-propyl)indole-6-carboxamide 2-(Methoxycarbonyl)indole-6-carboxylic acid was coupled with 2-amino-1,3-bis(t-butyldimethylsilyl)-1,3-propanediol by the method described above and the product purified by dry column chromatography (eluting with 1:4 EtOAc:petroleum ether) to give N-[1,3-bis(t-butyldimethylsilyloxy)-2-propyl]-2-(methoxycarbonyl)indole-6-carboxamide as a pale yellow foam (87%). Trituration with hot petroleum ether gave white needles, mp 127–129° C. $^1$H NMR (CDCl$_3$) δ9.24 (s, 1H, indole NH), 8.03 (s, 1H, H-3 or H-7), 7.72 (d, J=8.3 Hz, 1H, H-4), 7.43 (dd, J=8.3, 1.5 Hz, 1H, H-5), 7.24 (dd, J=1.9, 0.8 Hz, 1H, H-3 or H-7), 6.64 (d, J=8.3 Hz, 1H, amide NH), 4.26–4.18 (m, 1H, CONHCH), 3.97 (s, 3H, CO$_2$Me), 3.90 (dd, J=9.6, 3.5 Hz, 2H, CH$_2$O), 3.67 (dd, J=9.6, 6.4 Hz, 2H, CH$_2$O), 0.92 (s, 18H, $^t$Bu), 0.10 (s, 6 H, SiMe), 0.09 (s, 6H, SiMe); $^{13}$C NMR δ167.0. (CONH), 162.0 (CO$_2$Me), 136.4, 131.5, 129.6, 129.4 (C-2,6,8,9), 122.6, 118.5, 112.1, 108.5 (C-3,4, 5,7), 60.4 (CH$_2$O), 52.2, 51.9 (CONHCH, OCH$_3$), 25.9 (t-Bu), 18.2 (SiCMe$_3$), −5.4, −5.5 (SiMe$_2$). Anal. (C$_{26}$H$_{44}$N$_2$O$_5$Si$_2$) (*CRL 7726 coming).

A solution of N-[1,3-bis(t-butyldimethylsilyloxy)-2-propyl]-2-(methoxycarbonyl)indole-6-carboxamide (744 mg, 1.43 mmol) and tetrabutylammonium fluoride (2.9 mL of a 1M solution in THF, 2.9 mmol) in THF (20 mL) was stirred at 20° C. for 80 min and evaporated. The residue was crystallised from MeOH (10 mL) giving N-(1,3-dihydroxy-2-propyl)-2-(methoxycarbonyl)indole-6-carboxamide as a white solid (305 mg, 73%), mp 205–207° C. Dry column chromatography of the mother liquor (eluting with 20:1 EtOAc:MeOH) gave a second crop (57 mg, 14%). $^1$H NMR [(CD$_3$)$_2$SO] δ12.22 (s, 1H, indole NH), 7.97 (s, 1H, H-3 or H-7), 7.94 (d, J=8.0 Hz, 1H, amide NH), 7.70 (d, J=8.5 Hz, 1H, H-4), 7.59 (dd, J=8.5, 1.3 Hz, 1H, H-5), 7.20 (d, J=1.6 Hz, 1H, H-3 or H-7), 4.66 (t, J=5.7 Hz, 2H, OH), 4.03–3.95 (m, 1H, CONHCH), 3.90 (s, 3H, CO$_2$Me), 3.54 (t, J=5.8 Hz, 4H, CH$_2$OH). Anal. (C$_{14}$H$_{16}$N$_2$O$_5$) C,H,N.

N-(1,3-Dihydroxy-2-propyl)-2-(methoxycarbonyl) indole-6-carboxamide was hydrolysed by the method described above to give 2-carboxy-N-(1,3-dihydroxy-2-propyl)indole-6-carboxamide as a white solid (97%), mp 240–245° C. $^1$H NMR [(CD$_3$)$_2$SO] δ13.11 (br s, 1H, CO$_2$H), 12.05 (s, 1H, indole NH), 7.98 (s, 1H, H-3 or H-7), 7.92 (d, J=7.9 Hz, 1H, amide NH), 7.70 (d, J=8.5 Hz, 1H, H-4), 7.58 (d, J=8.5 Hz, 1H, H-5), 7.14 (s, 1H, H-3 or H-7), 4.4 (br s, 2H, OH), 4.08–3.92 (m, 1H, CONHCH), 3.56 (d, J=5.7 Hz, 4H, CH$_2$OH); $^{13}$C NMR δ166.8 (CONH), 162.5 (CO$_2$H), 136.5, 130.8, 130.5, 128.6 (C-2,6,8,9), 121.3, 118.9, 112.4, 107.0 (C-3,4,5,7), 60.4 (CH$_2$OH), 53.8 (CONHCH). Anal. (C$_{13}$H$_{14}$N$_2$O$_5$) (*CRL 7729 coming).

1-(t-Butoxycarbonyl)-3-(chloromethyl)-6-nitroindoline was coupled with 2-carboxy-N-(1,3-dihydroxy-2-propyl) indole-6-carboxamide by the method described above, the EtOAc layer dried (Na$_2$SO$_4$), evaporated, and the residue recrystallised from EtOH to give 2-[[3-(chloromethyl)-6-nitroindolin-1-yl]carbonyl]-N-(1,3-dihydroxy-2-propyl) indole-6-carboxamide as a cream powder (29%), mp 230–231° C. (dec.). $^1$H NMR [(CD$_3$)$_2$SO] δ12.13 (s, 1H, indole NH), 8.98 (d, J=2.1 Hz, 1H, H-7), 8.05 (dd, J=8.3, 2.2 Hz, 1H, H-5), 8.04 (s, 1H, H-3' or H-7'), 7.95 (d, J=8.0 Hz, 1H, amide NH), 7.76 (d, J=8.5 Hz, 1H, H-4'), 7.75 (d, J=8.3 Hz, 1H, H-4), 7.61 (dd, J=8.5, 1.4 Hz, 1H, H-5'), 7.29 (d, J=1.6 Hz, 1H, H-3' or H-7'), 4.87 (t, J=10.1 Hz, 1H, H-2), 4.70 (t, J=5.7 Hz, 2H, OH), 4.51 (dd, J=10.7, 5.1 Hz, 1H, H-2), 4.19–4.06 (m, 3H, H-3 and CH$_2$Cl), 4.04–3.97 (m, 1H, CONHCH), 3.55 (t, J=5.7 Hz, 4H, CH$_2$OH); $^{13}$C NMR δ166.8 (CONH), 160.4 (CON), 147.6, 144.6, 139.9, 135.7, 131.8, 131.0, 128.9 (C-6,8,9,2',6',8',9'), 125.5, 121.4, 119.4, 119.1, 112.2, 111.2, 106.1 (C-4,5,7,3',4',5',7'), 60.4 (CH$_2$OH), 54.0 (C-2), 53.8 (CONHCH), 47.0 (CH$_2$Cl), 42.0 (C-3). Anal. (C$_{22}$H$_{21}$ClN$_4$O$_6$).

EXAMPLE 7

Preparation of N-(carboxymethyl)-2-[[3-(chloromethyl)-6-nitroindolin-1-yl]carbonyl]indole-6-carboxamide 2-(Methoxycarbonyl)indole-6-carboxylic acid was coupled with glycine t-butyl ester hydrochloride in the presence of NaHCO$_3$ (1 equivalent) by the method described above to give N-[(butoxycarbonyl)methyl]-2-(methoxycarbonyl)indole-6-carboxamide as a white solid (86%), mp 181–183.5° C. (EtOAc). $^1$H NMR (CDCl$_3$) δ9.58 (s, 1H, indole NH), 8.06 (s, 1H, H-3 or H-7), 7.68 (d, J=8.4 Hz, 1H, H-4), 7.52 (dd, J=8.4, 1.5 Hz, 1H, H-5), 7.20 (dd, J=2.0, 0.8 Hz, 1H, H-3 or H-7), 6.82 (t, J=4.7 Hz, 1H, amide NH), 4.20 (d, J=5.0 Hz, 2H, CH$_2$), 3.96 (s, 3H, CO$_2$Me), 1.51 (s, 9H, t-Bu); $^{13}$C NMR δ169.5, 167.7, 162.1 (3×CO), 136.4, 130.6, 129.7, 129.5 (C-2,6,8,9), 122.5, 118.8, 112.3, 108.4 (C-3,4,5,7), 82.6 (OCMe$_3$), 52.2 (OCH$_3$), 42.7 (CONHCH$_2$), 28.1 (t-Bu). Anal. (C$_{17}$H$_{20}$N$_2$O$_5$) C,H,N.

A mixture of N-[(butoxycarbonyl)methyl]-2-(methoxycarbonyl)indole-6-carboxamide (0.94 g, 2.8 mmol) and LiOH.H$_2$O (0.19 g, 4.5 mmol) in THF (50 mL) and H$_2$O (15 mL) was stirred at 20° C. for 15 h then at 65° C. for 7 h, cooled, and the THF evaporated. EtOAc was added, the mixture extracted with aq. NaHCO$_3$, and the aqueous layer acidified. Extraction with EtOAc gave a mixture containing the required product and the corresponding diacid. Dry column chromatography (eluting with CHCl$_3$:EtOH 10:1) gave N-[(butoxycarbonyl)methyl]-2-carboxyindole-6-carboxamide as a white powder (97 mg, 11%), mp 267–268.5° C. $^1$H NMR [(CD$_3$)$_2$SO] δ13.15 (br s, 1H, CO$_2$H), 12.11 (s, 1H, indole NH), 8.82 (t, J=5.8 Hz, 1H, amide NH), 7.99 (s, 1H, H-3 or H-7), 7.71 (d, J=8.5 Hz, 1H, H-4), 7.56 (dd, J=8.5, 1.2 Hz, 1H, H-5), 7.13 (s, 1H, H-3 or H-7), 3.90 (d, J=5.8 Hz, 2H, CH$_2$), 1.43 (s, 9H, t-Bu). MS (DEI) m/z 318 (30%, M$^+$), 188 (100%); HRMS calcd. for C$_{16}$H$_{18}$N$_2$O$_5$ 318.12157, found 318.12136.

1-(t-Butoxycarbonyl)-3-(chloromethyl)-6-nitroindoline was coupled with N-[(butoxycarbonyl)methyl]-2-carboxyindole-6-carboxamide by the method described above and the product recrystallised from EtOAc to give with N-[(butoxycarbonyl)methyl]-2-[[3-(chloromethyl)-6-nitroindolin-1-yl]carbonyl]indole-6-carboxamide as a yellow solid (69%), mp 286° C. (dec.). $^1$H NMR [(CD$_3$)$_2$SO] δ12.20 (d, J=1.5 Hz, 1H, indole NH), 8.99 (d, J=2.2 Hz, 1H, H-7), 8.50 (t, J=6.0 Hz, 1H, amide NH), 8.06 (s, 1H, H-3' or H-7'), 8.05 (dd, J=8.2, 2.2 Hz, 1H, H-5), 7.78 (d, J=8.5 Hz, 1H, H-4'), 7.75 (d, J=8.2 Hz, 1H, H-4), 7.60 (dd, J=8.5, 1.4 Hz, 1H, H-5'), 7.30 (d, J=1.6 Hz, 1H, H-3' or H-7'), 4.87 (t, J=10.1 Hz, 1H, H-2), 4.51 (dd, J=10.7, 5.2 Hz, 1H, H-2), 4.19–4.08 (m, 3H, H-3 and $CH_2Cl$), 3.92 (d, J=5.9 Hz, 2H, $CONHCH_2$), 1.44 (s, 9H, t-Bu); $^{13}C$ NMR δ169.1 ($CO_2tBu$), 167.1 (CONH), 160.4 (CON), 147.6, 144.6, 140.0, 135.7, 132.0, 130.0, 129.2 (C-6,8,9,2',6',8',9'), 125.5, 121.7, 119.4, 118.9, 112.2, 111.2, 106.1 (C-4,5,7,3',4',5',7'), 80.5 ($OCMe_3$), 54.0 (C-2), 47.0 ($CH_2Cl$), 42.0 (C-3), 41.9 ($CH_2CO_2tBu$), 27.7 (t-Bu). Anal. ($C_{25}H_{25}ClN_4O_6$) C, H, N.

A suspension of N-[(butoxycarbonyl)methyl]-2-[[3-(chloromethyl)-6-nitroindolin-1-yl]carbonyl)indole-6-carboxamide (70 mg, 0.14 mmol) in HCl-saturated dioxane (20 mL) was stirred at 20° C. for 2 h, most of the dioxane evaporated, and the residue triturated with hot EtOAc to give N-(carboxymethyl)-2-[[3-(chloromethyl)-6-nitroindolin-1-yl]carbonyl]indole-6-carboxamide as a pale yellow powder (50 mg, 80%), mp 281° C. (dec.). $^1H$ NMR [$(CD_3)_2SO$] δ12.57 (br s, 1H, $CO_2H$), 12.20 (d, J=1.3 Hz, 1H, indole NH), 8.99 (d, J=2.2 Hz, 1H, H-7), 8.84 (t, J=5.9 Hz, 1H, amide NH), 8.07 (s, 1H, H-3' or H-7'), 8.05 (dd, J=8.3, 2.2 Hz, 1H, H-5), 7.79 (d, J=8.4 Hz, 1H, H-4'), 7.75 (d, J=8.3 Hz, 1H, H-4), 7.61 (dd, J=8.4, 1.3 Hz, 1H, H-5'), 7.30 (d, J=1.9 Hz, 1H, H-3' or H-7'), 4.87 (t, J=10.1Hz, 1H, H-2), 4.51 (dd, J=10.7, 5.2 Hz, 1H, H-2), 4.19–4.08 (m, 3H, H-3 and $CH_2Cl$), 3.95 (d, J=5.8 Hz, 2H, $CONHCH_2$). Anal. ($C_{23}H_{17}ClN_4O_6$) C, H, N.

EXAMPLE 8

Preparation of dimethyl 2-(S,R)-[N-[3-(S,R)-(chloromethyl)-1-[(5',6',7'-trimethoxyindol-2'-yl) carbonyl]indolin-6-yl]ureylene]pentanedicarboxylic acid A solution of dimethyl (S)-2-isocyanatopentanedioate (116 mg, 0.58 mmol) [prepared by the method of J. S. Nowick, N. A. Powell, T. M. Nguyen and G. Noronha, *J. Org. Chem.*, (1992), 57, 7364] in dry THF (1 mL) was added to a stirred solution of 6-amino-3-(chloromethyl)-1-[(5',6', 7'-trimethoxyindol-2'-yl)carbonyl]indolin (228 mg, 0.55 mmol) in dry THF (8 mL) at 20° C. TLC analysis after 40 min indicated incomplete reaction. More isocyanate (0.33 g, 1.6 mmol) in THF (1 mL) was added, and after a further 20 min the reaction was quenched by the addition of $H_2O$ (10 mL) and stirred overnight. The THF was evaporated, the aqueous residue extracted with EtOAc, and the organic layer dried ($Na_2SO_4$) and evaporated. Column chromatography (eluting with 3:1 EtOAc:petroleum ether) gave a mixture ($^1H$ NMR) of the urea derived from (S)-glutamic acid dimethyl ester and the desired dimethyl 2-(S)-[N-[3-(S,R)-(chloromethyl)-1-[(5',6',7'-trimethoxyindol-2'-yl)carbonyl] indolin-6-yl)ureylene]pentanedioate (ca. 280 mg, ca. 80%) as a pale yellow solid.

This mixture was dissolved in MeOH (20 mL), a solution of cesium carbonate (3.3 g, ca. 10 mmol) in $H_2O$ (5 mL) added, and the yellow solution stirred at 20° C. for 24 h. The mixture was washed with EtOAc, the aqueous layer acidified (2N HCl), extracted with EtOAc (x2), and the extracts dried ($Na_2SO_4$) and evaporated. Crystallisation from EtOAc—MeOH gave 2-(S,R)-[N-[3-(S,R)-(chloromethyl)-1-[(5',6',7'-trimethoxyindol-2'-yl) carbonyl]indolin-6-yl] ureylene]pentanedicarboxylic acid as an off-white powder (108 mg, 33% for two steps), mp 173–174° C. (dec.). $^1H$ NMR [$(CD_3)_2SO$] δ12.48 (br s, 2H, $CO_2H$), 11.42 (d, J=1.5 Hz, 1H, indole NH), 8.75 (s, 1H, NH), 8.13 (s, 1H, H-7), 7.28 (s, 2H, H-4,5), 7.01 (d, J=2.2 Hz, 1H, H-3'), 6.96 (s, 1H, H-4'), 6.40 (d, J=8.0 Hz, 1H, NH), 4.61 (dd, J=10.9, 8.4 Hz, 1H, H-2), 4.26 (dd, J=10.9, 4.4 Hz, 1H, H-2), 4.26–4.18 (m, 1H, $CHCO_2H$), 4.01–3.94 (m, 1H, $CHCH_2Cl$), 3.93 (s, 3H, $OCH_3$), 3.84–3.78 (m, 2H, $CHCH_2Cl$), 3.82 (s, 3H, $OCH_3$), 3.79 (s, 3H, $OCH_3$), 2.38–2.22 (m, 2H, $CH_2CH_2CO_2H$), 2.06–1.97 (m, 1H, $CH_2CH_2CO_2H$), 1.86–1.76 (m, 1H, $CH_2CH_2CO_2H$); $^{13}C$ NMR δ173.9, 173.6 (2x$CO_2H$), 160.1 (amide carbonyl), 154.7, 149.1, 143.9, 140.2, 139.8, 139.0, 130.9, 125.2, 124.7, 123.1 (urea carbonyl, C-6,8,9,2',5',6', 7',8',9'), 124.5, 113.1, 106.8, 105.9, 98.0 (C-4,5,7,3',4'), 61.0, 60.9, 55.9 (3x$OCH_3$), 54.3 (C-2), 51.5 ($CHCO_2H$), 47.7 ($CH_2Cl$), 41.8 (C-3), 29.9, 27.2 ($CH_2CH_2CO_2H$). Anal. ($C_{27}H_{29}ClN_4O_9$.0.5$H_2O$) C,H,N.

EXAMPLE 9

Biological Activity

The compounds of Examples 1 and 3 show potent cytotoxicity to mammalian tumour cells, and are thus of interest as anticancer drugs. The free amine (compound of Example 1) shows potent cytotoxicity to mammalian tumour cells, and is thus of interest as an anticancer drug. It has an $IC_{50}$ in AA8 cells of 0.32 μM, and against UV4 cells of 0.059 μM. The corresponding prodrug (of Example 3) is expectedly much less cytotoxic (an $IC_{50}$ in AA8 cells of 23 μM and against UV4 cells of 19.6 μM). For these evaluations, AA8 and UV4 cells were maintained in exponential phase growth (doubling times 14 and 15 h respectively) using Alpha MEM containing fetal calf serum (10% v/v) without antibiotics, and were subcultured twice weekly by trypsinization. Bulk cultures were prepared for experiments by seeding cells in spinner flasks at $10^4$ cells/mL in the above medium with addition of penicillin (100 IU/mL) and streptomycin (100 μg/mL). Cultures were initiated in 96-well microtiter trays to give 200 (AA8) or 300 (UV4) cells in 0.05 mL per well. After growth in a $CO_2$ incubator for 24 h, drugs were added in culture medium, using serial two-fold dilutions to provide duplicate cultures at five different concentrations for each of eight drugs (plus eight controls) per tray. After 18 h drugs were removed by washing cultures three times with fresh medium, and the trays were incubated for a further 78 h. Cell density was then determined by staining with methylene blue as described [Finlay, G. J.; Baguley, B. C; Wilson, W. R. Anal. Biochem., 1984, 139, 272–277]. The $IC_{50}$ was calculated as the drug concentration providing 50% inhibition of growth relative to the controls.

EXAMPLE 10

Activation of Prodrug by Nitroreductase

The compound of the formula (II) produced in example 3 also shows high levels of activation by the isolated *E. coli* NR2 nitroreductase enzyme, as shown by the following experiment.

The compound was incubated with UV4 cells for 18 hours in 96-well plates under aerobic conditions. The UV4 cell line is a mutant Chinese hamster ovary fibroblast lines derived from the wild-type AA8. It is a UV complementation group 1 mutant, with a defect in the incision step of excision repair [Thompson, L. H. et al Proc. Natl. Acad. Sci (USA), 1980, 78, 3734; Thompson, L. H.; Carrono, A. V. In Cellular responses to DNA Damage, UCLA Symposium on Molecular and Cellular Biology, New Series, Vol. 11 (Freidberg, E. C.; Bridges, B. R.; Eds), Alan R. Liss: New York, 1983: p 125], and is highly sensitive to agents which form bulky DNA monoadducts or crosslinks [Hoy, C.A . et al Cancer Res., 1985, 45, 1737–1747]. The $IC_{50}$ of the compound was determined as described above in Example 9 and found to be 11.9 μM.

The experiment was repeated but in addition purified *E. coli* nitroreductase enzyme (1 μg/mL) and NADH (1 mM, as cofactor) was added during the entire time of the incubation.

The $IC_{50}$ was determined and found to be 0.46 μM. This represents a 26-fold activation by the enzyme.

A similar set of experiments on the compound of formula (I) produced in example 1(h) also showed significant activation ($IC_{50}$ 2.34 μM in the absence of *E.coli* nitroreductase, $IC_{50}$ 0.006 μM in the presence of *E.coli* nitroreductase, representing a 400-fold activation by the enzyme.

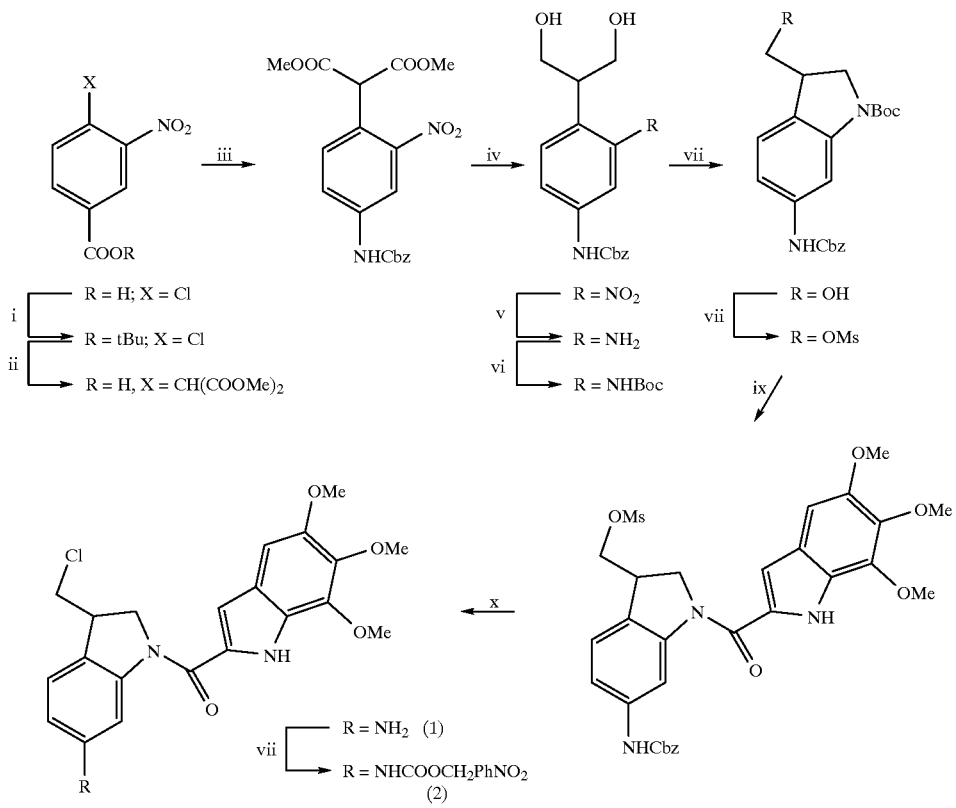

Scheme 1 i   SOCl₂, then KOtBu
ii  NaH/CH₂(COOMe)₂, then HCOOH
iii SOCl₂, then NaN₃, then PhCH₃/heat/PhCH₂OH
iv  iBu₂AlH
v   PtO₂/H₂
vi  (Boc)₂O/Na₂CO₃
vii DEAD/PPh₃
viii MsCl/Et₃N
ix  HCl, then EDCl/5, 6, 7-triOMeindole-2-carboxylic acid
x   Pd — C/H₂/NH₄⁺HCO₂⁻, then LiCl
xi  4-NO₂PhCH₂OCOCl

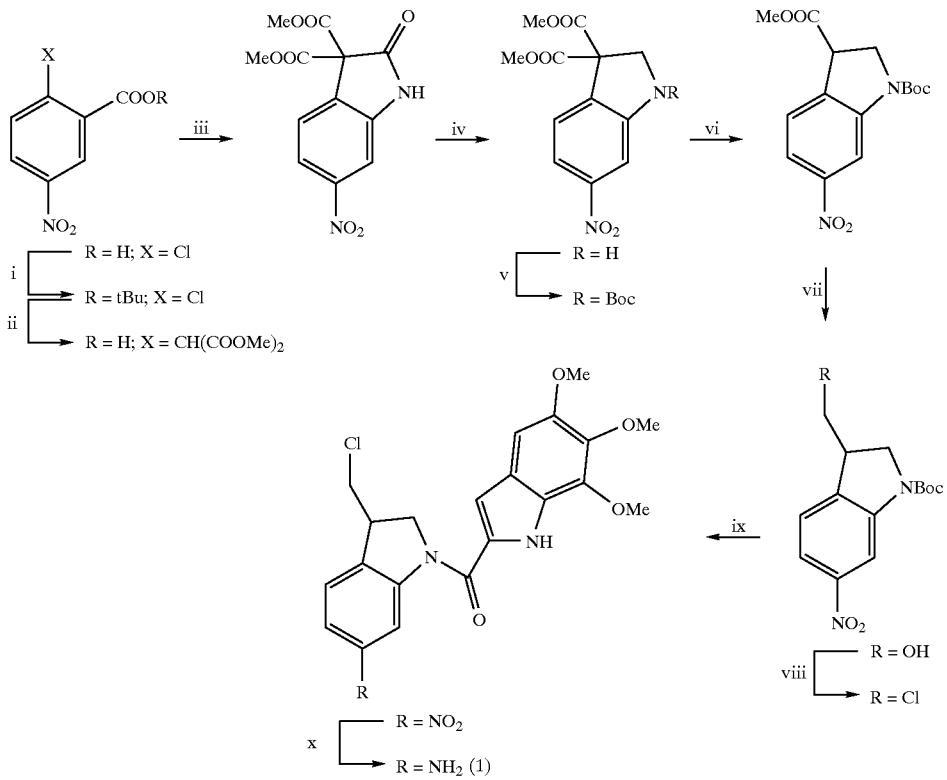

Scheme 2 i  SOCl₂ then KOtBu
ii  NaH/CH₂(COOMe)₂ then HCOOH
iii  (PhO)₂PON₃/Et₃N
iv  BH₃·DMS
v  (Boc)₂O/DMAP
vi  NaOMe then CF₃CO₂H
vii  iBu₂AlH
viii  MsCl/Et₃N then LiCl
ix  HCl then EDCI/5,6,7-triOMeindole-2-carboxylic acid
x  PtO₂/H₂

We claim:

1. A compound of the formula (I):

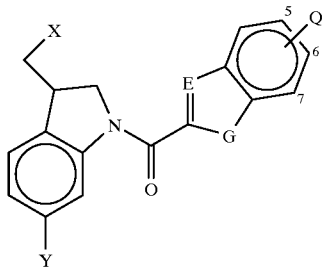

(I)

wherein:

X is halogen or $OSO_2R$, where R represents hydrogen or lower straight or branched alkyl of up to five carbon atoms optionally substituted with from 1 to 4 hydroxyl, acid, or amino groups which amino groups are optionally substituted by one or two lower alkyl groups;

Y is $NH_2$, $NO_2$, NHOH, NHR, NRR, N(O)RR, NROH, where R is defined as above;

E is —CH═;

G is NH; and

Q is from one to three of H, OR, NRR, CONHR, NHCOR or NHCONHR at any one of positions 5 to 7 where R is defined as above, which may be the same or different when Q is two or three, a group of formula (Ia):

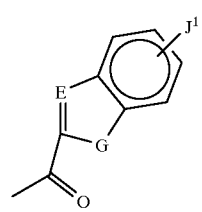

(Ia)

where E and G are as defined above, $J^1$ is up to three groups, H, OR or NRR, which may be the same or different when $J^1$ is two or three, where R is as defined above, or is a group of the formula —$CONHJ^2$, —$NHJ^2$ or $OJ^2$ where $J^2$ is a group —$(CH_2)_m$Ht where m is an integer from 1 to 4 and Ht is a carbon ring or heterocyclic ring containing 5 or 6 atoms, one or two of which may be oxygen, sulphur or nitrogen, the remainder being carbon;

or a physiologically functional derivative thereof.

2. A compound according to claim 1 wherein X is chloro.

3. A compound according to claim 1 wherein Q represent three methoxy groups at positions 5, 6 and 7 of the indol grouping.

4. 6-Amino-3-(chloromethyl)-1-[(5',6',7'-trimethoxyindol-2'-yl)carbonyl]indoline or a physiologically functional derivative thereof.

5. 2-[[3-(chloromethyl)-6-nitroindolin-1-yl]carbonyl]-N-[2-(2-pyridinyl)ethyl]indole-6-carboxamide or a physiologically functional salt thereof.

6. 2-[[3-(chloromethyl)-6-nitroindolin-1-yl]carbonyl]-N-[2-(4-morpholinyl)ethyl]indole-6-carboxamide or a physiologically functional salt thereof.

7. 2-[[3-(chloromethyl)-6-nitroindolin-1-yl]carbonyl]-N-[1,3-dihydroxy-2-propyl]indole-6-carboxamide.

8. N-(carboxymethyl)-2-[[3-chloromethyl)-6 nitroindolin-1-yl]carbonylindole-6-carboxamide.

9. A composition comprising a compound according to claim 1 together with a pharmaceutically acceptable carrier or diluent.

10. A method of treating a mammalian tumor cell which comprises administering to a patient in need of treatment an effective amount of a compound according to claim 1.

11. A compound according to claim 3 wherein Q represent three methoxy groups at positions 5, 6 and 7 of the indol grouping.

12. A method of treating a mammalian tumor cell which comprises administering to a patient in need of treatment an effective amount of a compound according to claim 2.

* * * * *